(12) United States Patent
Collin et al.

(10) Patent No.: US 7,196,171 B2
(45) Date of Patent: Mar. 27, 2007

(54) ALSTRÖEM SYNDROME GENE, GENE VARIANTS, EXPRESSED PROTEIN AND METHODS OF DIAGNOSIS FOR ALSTRÖEM SYNDROME

(75) Inventors: Gayle B. Collin, Trenton, ME (US); Jan Marshall, Mount Desert, ME (US); Mitchell L. Martin, Vverona, NJ (US); Juergen K. Naggert, Bar Harbor, ME (US); Patsy M. Nishina, Bar Harbor, ME (US); W. Venus So, Nutley, NJ (US)

(73) Assignees: Hoffmann-La Roche Inc., Nutley, NJ (US); The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 10/973,045

(22) Filed: Oct. 20, 2004

(65) Prior Publication Data

US 2005/0214794 A1 Sep. 29, 2005

Related U.S. Application Data

(62) Division of application No. 10/292,576, filed on Nov. 12, 2002, now abandoned.

(60) Provisional application No. 60/345,883, filed on Nov. 9, 2001.

(51) Int. Cl.
*C07K 14/00* (2006.01)
*C07H 21/04* (2006.01)
*A61K 38/00* (2006.01)

(52) U.S. Cl. ............... 530/350; 536/23.1; 514/12

(58) Field of Classification Search .......... 530/350; 514/12; 435/69.1; 536/23.1
See application file for complete search history.

(56) References Cited

FOREIGN PATENT DOCUMENTS

| WO | WO 94/20079 | 9/1994 |
|----|----|----|
| WO | WO 01/79443 | 10/2001 |
| WO | WO 01/79449 | 10/2001 |
| WO | WO 01/79449 A2 * | 10/2001 |
| WO | WO 03/034072 A2 | 4/2003 |
| WO | WO 01/22920 A2 * | 4/2006 |

OTHER PUBLICATIONS (Accession No. AAG74901, A_Geneseq_21).*
(Accession No. AAU32140, A_Geneseq_21).*
Michaud et al., J. Ped., 128, pp. 225-229 (1996).
Collin et al., Hum. Mol. Genet., 6, pp. 213-219 (1997).
Collin et al., Hum. Genet., 105, pp. 474-479 (1999).
Macari et al., Hum. Genet., 103, pp. 658-661 (1998).
Kopelman, P. G., Nature, 404, pp. 635-643 (2000).
Froguel et al., Recent Prog. Horm. Res., 56, pp. 91-105 (2001).
Slavotinek et al., Nat. Genet., 26, pp. 15-16 (2000).
Mykytyn et al., Nat. Genet., 28, pp. 188-191 (2001).
Nishimura et al., Hum. Mol. Genet., 10, pp. 865-874 (2001).
Inui, A., Trends Neurosci., 22, 62-67 (1999).
Collin et al., Genomics, 37., pp. 125-130 (1996).
Nishina et al., Genomics, 54, pp. 215-220 (1998).
Rastogi, P., Methods Mol. Biol., 132, pp. 47-69 (2000).
Gloyn et al., Best Pract. Res. Clin. Endocrinol. Metab., 15, pp. 293-308 (2001).
Boutin et al., Best Pract. Res. Clin. Endocrinol. Metab., 15, pp. 391-404 (2001).
Connolly et al., Am. J. Med. Genet., 40, pp. 421-424 (1991).
Marshall et al., Am. J. Med. Genet., 73, pp. 150-161 (1997).
Goldstein et al., Medicine Baltimore, 52, pp. 53-71 (1973).
Charles et al., J. Med. Genet., 27, pp. 590-592 (1990).
Naggert et al., Curr. Opp. Genet. Dev., 7, pp. 398-404 (1997).
Kunkel et al., Proc. Natl. Acad. Sci. USA, 74, pp. 1245-1249 (1977).
Alstrom et al., Acta Psychiatr. Neurol. Scand., 34 (Supplement 129), 1-35 (1959).
Ohara et al, DNA Res, vol. 4 pp. 141-150 (1997).
Collin et al, Nature Genet., 31 74-78 (2002).
Hearn et al, Nature Genet. 31, 79-83 (2002).
Chen et al, Genomics, 74 219-227 (2001).
Nili et al, J. Endocrin. Genet. 2, 29-35 (2001).
Nagase,T. et al, Database XP-002285134 (1997).
Isogai, T. et al, Database XP-002285135 (2000).
Hearn, T. et al, Database XP-002285136 (2002).

* cited by examiner

*Primary Examiner*—Robert B. Mondesi
(74) *Attorney, Agent, or Firm*—George W. Johnston; Patricia S. Rocha-Tramaloni

(57) ABSTRACT

The present invention relates to a nucleic acid sequence linked to Alström syndrome, variants of that nucleic acid sequence, the protein produced by that nucleic acid sequence and screening methods for testing individuals to determine if they are carriers of Alström syndrome.

1 Claim, 20 Drawing Sheets

```
mALMS              1704 TLQESLQLHRPDFISHSGERIKRLKLLVQERKLQSLFQS-EREALFHSAR 1752
hALMS              1770 TLQESLQFHRPDFISRSGERIKRLKLIVQERKLQSMLQT-ERDALFNIDR 1818
macaque AB055273    562 TLQEALEVRKPQFISRSQERLKKLEHMVQQRKAQRKEDLRQKQSILPIRT  611
mouse AK016590      194 TLQEALEVHRPQFISRSQERLQKLKRMVQQRKTQQKESLGQKQSLLPVRA  243
                        ****.*. ..* ***.* **...* .**.** *        .. ..

mALMS              1753 ----------PLPRRVLLAVQKNKPIGKKEMIQRTRRIYEQLPEVKKKRE 1792
hALMS              1819 ERQGHQNRMCPLPKRVFLAIQKNKPISKKEMIQRSKRIYEQLPEVQKKRE 1868
macaque AB055273    612 SKK---QFTVPHPLSDNLFKPKERCISEKEMHMRSKRIYNNLPE       652
mouse AK016590      244 NKK---QFTIPHPLSDNLFKPKERCISEKEMHMRSKRIYNNLPEVKKKKE  290
                         *  *      * . * *** *..* ...* mALMS              1793 EEKRKSEYKSYRLRAQHYKMKVTNHLLGRKV       1823
hALMS              1869 EEKRKSEYKSYRLRAQLYKKRVTNQLLGRKV       1899
macaque AB055273
mouse AK016590      291 EQKKRMILQSNRLRAEVFKKQLLDQLLQRNA       321
                        *.*.. ...* ****. .* ..  .** *
```

```
agtaaaggtattctaaagatttcagctgtccctgaactaactgatgtgaatactggaaaaccagtatctctctct  75
agttcttattttcacagagagaaatcgaatattttcagtccacaggaattgccaggtagtcatgtaactgaagat
150
gtgctgaaggtttcaacaattcctggaccagctggccagaaaacagtattaccaacagctcttcctagttccttt
225
tcacatcgagagaaaccagatattttctatcaaaaggatttgccagatagacatctaactgaagatgctctaaag
300
atctcaagtgctcttgggcaagctgatcaaattaccggattacaaacagttccctctggtacttactcacatggt
375
gagaatcacaagcttgtttcagaacatgtccaaaggctaatagatatttgaattcttctgactccagtgttagct
450
caaataatgtgcttttaaattctcaggctgatgacagagttgtaataaataaaccagaatctgcaggttttagag
525
atgttggctctgaagaaatccaggatgcagaaaatagtgctaaaactcttaaggaaattcggacacttttgATGG
600
                                                                          M
1
AGGCAGAAAATATGGCACTGAAACGATGCAATTTTCCTGCTCCCCTTGCCCGTTTCAGAGATATTAGTGATATTT
675
 E  A  E  N  M  A  L  K  R  C  N  F  P  A  P  L  A  R  F  R  D  I  S  D  I
26
CATTTATACAATCTAAGAAGGTGGTTTGCTTCAAAGAACCCTCTTCCACGGGTGTATCTAATGGTGATTTGCTTC
750
 S  F  I  Q  S  K  K  V  V  C  F  K  E  P  S  S  T  G  V  S  N  G  D  L  L
51
ACAGACAGCCATTCACAGAGGAAAGCCCAAGCAGCAGGTGCATACAGAAGGATATTGGCACACAGACGAATTTGA
825
 H  R  Q  P  F  T  E  E  S  P  S  S  R  C  I  Q  K  D  I  G  T  Q  T  N  L
76
AATGCCGGAGAGGCATTGAAAATTGGGAGTTTATTAGTTCAACTACAGTTAGAAGTCCTCTACAGGAAGCAGAGA
900
 K  C  R  R  G  I  E  N  W  E  F  I  S  S  T  T  V  R  S  P  L  Q  E  A  E
101
GCAAAGTCAGTATGGCATTAGAAGAAACTCTTAGGCAATATCAAGCAGCCAAATCTGTAATGAGGTCTGAACCTG
975
 S  K  V  S  M  A  L  E  E  T  L  R  Q  Y  Q  A  A  K  S  V  M  R  S  E  P
126
```

```
AAGGGTGTAGTGGAACCATTGGGAATAAAATTATTATCCCTATGATGACTGTCATAAAAAGTGATTCAAGTAGTG
1050
 E  G  C  S  G  T  I  G  N  K  I  I  I  P  M  M  T  V  I  K  S  D  S  S  S
151
ATGCCAGTGATGGAAATGGTTCCTGCTCGTGGGACAGTAATTTACCAGAGTCTTTGGAATCAGTTTCTGATGTTC
1125
 D  A  S  D  G  N  G  S  C  S  W  D  S  N  L  P  E  S  L  E  S  V  S  D  V
176
TTCTAAACTTCTTTCCATATGTTTCACCCAAGACAAGTATAACAGATAGCAGGGAGGAAGAGGGTGTGTCAGAGA
1200
 L  L  N  F  F  P  Y  V  S  P  K  T  S  I  T  D  S  R  E  E  E  G  V  S  E
201
GTGAGGATGGTGGTGGTAGCAGTGTAGATTCACTGGCTGCACATGTGAAAAACCTTCTGCAATGTGAATCCTCAC
1275
 S  E  D  G  G  G  S  S  V  D  S  L  A  A  H  V  K  N  L  L  Q  C  E  S  S
226
TGAATCATGCTAAAGAAATACTCAGAAATGCAGAGGAAGAGGAAAGCCGGGTACGAGCACATGCCTGGAATATGA
1350
 L  N  H  A  K  E  I  L  R  N  A  E  E  E  E  S  R  V  R  A  H  A  W  N  M
251
AGTTCAATTTAGCACATGATTGTGGATACTCCATTTCAGAATTAAATGAAGATGACAGGAGGAAAGTAGAAGAGA
1425
 K  F  N  L  A  H  D  C  G  Y  S  I  S  E  L  N  E  D  D  R  R  K  V  E  E
276
TCAAGGCAGAGTTATTTGGTCATGGAAGAACAACTGACTTGTCCAAGGGTTTACAGAGTCCACGGGGAATGGGAT
1500
 I  K  A  E  L  F  G  H  G  R  T  T  D  L  S  K  G  L  Q  S  P  R  G  M  G
301
GCAAGCCAGAAGCTGTATGTAGTCACATTATTATTGAGAGCCATGAAAAGGGATGTTTCCGGACTCTAACTTCTG
1575
 C  K  P  E  A  V  C  S  H  I  I  I  E  S  H  E  K  G  C  F  R  T  L  T  S
326
AACATCCACAACTAGATAGACACCCTTGTGCTTTCAGATCTGCTGGACCCTCAGAAATGACCAGAGGACGGCAGA
1650
 E  H  P  Q  L  D  R  H  P  C  A  F  R  S  A  G  P  S  E  M  T  R  G  R  Q
351
```

Fig. 6-2

```
ACCCATCATCATGCAGAGCCAAGCATGTCAACCTTTCTGCATCCTTAGACCAGAACAACTCCCATTTCAAAGTTT
1725
```

Fig. 6-2

ACCCATCATCATGCAGAGCCAAGCATGTCAACCTTTCTGCATCCTTAGACCAGAACAACTCCCA
TTTCAAAGTTT 1725
N   P   S   S   C   R   A   K   H   V   N   L   S   A   S   L   D   Q   N   N   S   H
F   K   V   376
GGAATTCCTTGCAGTTAAAAAGTCATTCCCCATTTCAGAACTTTATACCTGATGAATTCAAAAT
CAGCAAAGGTC 1800
W   N   S   L   Q   L   K   S   H   S   P   F   Q   N   F   I   P   D   E   F   K   I
S   K   G   401
TTCGAATGCCATTCGATGAAAAGATGGACCCTTGGCTGTCAGAATTAGTAGAACCTGCTTTTGT
GCCACCTAAAG 1875
L   R   M   P   F   D   E   K   M   D   P   W   L   S   E   L   V   E   P   A   F   V
P   P   K   426
AAGTGGATTTTCATTCTTCATCACAAATGCCGTCCCCAGAACCCATGAAAAAGTTTACTACCTC
CATCACTTTTT 1950
E   V   D   F   H   S   S   S   Q   M   P   S   P   E   P   M   K   K   F   T   T   S
I   T   F   451
CATCTCACCGACATTCTAAATGCATTTCCAATTCCTCTGTTGTTAAGGTTGGTGTTACTGAAGG
TAGCCAGTGTA 2025
S   S   H   R   H   S   K   C   I   S   N   S   S   V   V   K   V   G   V   T   E   G
S   Q   C   476
CTGGAGCATCTGTGGGGGTATTTAATTCTCATTTCACTGAAGAACAAAATCCTCCCAGAGATCT
TAAACAGAAAA 2100
T   G   A   S   V   G   V   F   N   S   H   F   T   E   E   Q   N   P   P   R   D   L
K   Q   K   501
CCTCTTCCCCTTCATCATTTAAAATGCATAGTAATTCACAAGATAAAGAAGTGACTATTTTAGC
AGAAGGTAGAA 2175
T   S   S   P   S   S   F   K   M   H   S   N   S   Q   D   K   E   V   T   I   L   A
E   G   R   526
GGCAAAGCCAAAAATTACCTGTTGATTTTGAGCGTTCTTTTCAAGAAGAAAAACCCTTAGAAAG
ATCAGATTTTA 2225

Fig. 6-2 (continuation)

```
R  Q  S  Q  K  L  P  V  D  F  E  R  S  F  Q  E  E  K  P  L  E  R
S  D  F     551
CAGGCAGTCATTCTGAGCCCAGTACCAGGGCAAATTGTAGCAATTTCAAGGAAATTCAGATTTC
TGATAACCATA 2325
T  G  S  H  S  E  P  S  T  R  A  N  C  S  N  F  K  E  I  Q  I  S
D  N  H     576
CCCTTATTAGCATGGGCAGACCAAGTTCCACCCTAGGAGTAAACAGATCGAGTTCCAGACTAGG
AGTAAAAGAGA 2400
T  L  I  S  M  G  R  P  S  S  T  L  G  V  N  R  S  S  R  L  G
V  K  E     601
AGAATGTAACTATAACTCCAGATCTTCCTTCTTGCATTTTTCTTGAACAACGAGAGCTCTTTGA
ACAAAGCAAAG 2475
K  N  V  T  I  T  P  D  L  P  S  C  I  F  L  E  Q  R  E  L  F  E
Q  S  K     626
CCCCACGTGCAGATGACCATGTGAGGAAACACCATTCTCCCTCTCCTCAACATCAGGATTATGT
AGCTCCAGACC 2550
A  P  R  A  D  D  H  V  R  K  H  H  S  P  S  P  Q  H  Q  D  Y  V
A  P  D     651
TTCCTTCTTGCATTTTTCTTGAACAACGAGAACTCTTTGAACAGTGCAAAGCCCCATATGTAGA
TCATCAAATGA 2625
L  P  S  C  I  F  L  E  Q  R  E  L  F  E  Q  C  K  A  P  Y  V  D
H  Q  M     676
GAGAAAACCATTCTCCCCTTCCTCAAGGTCAGGATTCTATAGCTTCAGACCTTCCGTCTCCCAT
TTCTCTTGAAC 2700
R  E  N  H  S  P  L  P  Q  G  Q  D  S  I  A  S  D  L  P  S  P  I
S  L  E     701
AATGCCAAAGCAAAGCGCCAGGTGTAGATGACCAAATGAATAAACACCATTTTCCCCTTCCTCA
AGGTCAGGATT 2775
Q  C  Q  S  K  A  P  G  V  D  D  Q  M  N  K  H  H  F  P  L  P  Q
G  Q  D     726
```

Fig. 6-2 (continuation)

```
GTGTAGTGGAAAAGAATAATCAACATAAGCCTAAATCACACATTTCTAATATAAATGTTGAAGC
CAAGTTCAATA 2850
C   V   V   E   K   N   N   Q   H   K   P   K   S   H   I   S   N   I   N   V   E   A
K   F   N   751
CTGTGGTCTCCCAGTCAGCCCCAAATCACTGTACATTAGCAGCATCTGCATCTACTCCTCCTTC
AAATAGAAAAG 2925
T   V   V   S   Q   S   A   P   N   H   C   T   L   A   A   S   A   S   T   P   P   S
N   R   K   776
CACTTTCTTGTGTTCATATAACTCTTTGTCCCAAGACTTCTTCCAAGTTGGATAGTGGAACTTT
AGATGAAAGAT 3000
A   L   S   C   V   H   I   T   L   C   P   K   T   S   S   K   L   D   S   G   T   L
D   E   R   801
TCCATTCATTGGATGCTGCTTCTAAAGCGAGGATGAATAGTGAGTTTAACTTTGACTTACATAC
TGTATCTTCGA 3075
F   H   S   L   D   A   A   S   K   A   R   M   N   S   E   F   N   F   D   L   H   T
V   S   S   826
```

Fig. 6-3

```
GATCACTGGAACCAACCTCCAAATTATTGACCAGTAAACCTGTAGCACAGGATCAAGAATCTTT
AGGTTTTCTAG 3150
 R   S   L   E   P   T   S   K   L   L   T   S   K   P   V   A   Q   D   Q   E   S   L
 G   F   L   851
GACCTAAATCTTCACTGGATTTCCAAGTCGTACAGCCTTCTCTTCCAGACAGTAACACTATTAC
TCAGGACTTGA 3225
 G   P   K   S   S   L   D   F   Q   V   V   Q   P   S   L   P   D   S   N   T   I   T
 Q   D   L   876
AAACCATACCTTCTCAGAATAGCCAGATAGTAACCTCCAGGCAAATACAAGTGAACATTTCAGA
TTTCGAAGGAC 3300
 K   T   I   P   S   Q   N   S   Q   I   V   T   S   R   Q   I   Q   V   N   I   S   D
 F   E   G   901
ATTCCAATCCAGAGGGGACCCCAGTATTTGCAGATCGATTACCAGAGAAGATGAAGACCCCACT
TTCTGCTTTCT 3375
 H   S   N   P   E   G   T   P   V   F   A   D   R   L   P   E   K   M   K   T   P   L
 S   A   F   926
CTGAAAAATTGTCATCTGATGCAGTCACTCAGATAACAACAGAAAGTCCAGAAAAGACCCTATT
TTCATCTGAGA 3450
 S   E   K   L   S   S   D   A   V   T   Q   I   T   T   E   S   P   E   K   T   L   F
 S   S   E   951
TTTTTATTAATGCTGAAGATCGTGGACATGAAATTATAGAGCCTGGTAACCAGAAGCTACGCAA
AGCTCCTGTCA 3525
 I   F   I   N   A   E   D   R   G   H   E   I   I   E   P   G   N   Q   K   L   R   K
 A   P   V   976
AGTTTGCCTCATCATCTTCAGTCCAACAGGTTACTTTTTCTCGCGGCACAGATGGCCAGCCTTT
ATTATTGCCAT 3600
 K   F   A   S   S   S   S   V   Q   Q   V   T   F   S   R   G   T   D   G   Q   P   L
 L   L   P   1001
ATAAGCCTTCTGGTAGTACCAAGATGTATTATGTTCCACAATTAAGACAAATTCCTCCATCTCC
GGATTCCAAAT 3675
```

Fig. 6-3 (continuation)

```
Y  K  P  S  G  S  T  K  M  Y  Y  V  P  Q  L  R  Q  I  P  P  S  P
D  S  K     1026
CAGATACCACCGTTGAAAGCTCCCATTCAGGATCCAATGATGCCATTGCTCCAGACTTCCCAGC
TCAGGTGCTAG 3750
S  D  T  T  V  E  S  S  H  S  G  S  N  D  A  I  A  P  D  F  P  A
Q  V  L     1051
GCACAAGAGATGATGACCTCTCAGCCACTGTTAACATTAAACATAAAGAAGGAATCTACAGTAA
GAGGGTAGTGA 3825
G  T  R  D  D  D  L  S  A  T  V  N  I  K  H  K  E  G  I  Y  S  K
R  V  V     1076
CTAAGGCATCCTTGCCAGTGGGAGAAAAACCCTTGCAGAATGAAAATGCAGATGCCTCAGTTCA
AGTGCTAATCA 3900
T  K  A  S  L  P  V  G  E  K  P  L  Q  N  E  N  A  D  A  S  V  Q
V  L  I     1101
CTGGGGATGAGAACCTCTCAGACAAAAAACAGCAAGAGATTCACAGTACAAGGGCAGTGACTGA
GGCTGCCCAGG 3975
T  G  D  E  N  L  S  D  K  K  Q  Q  E  I  H  S  T  R  A  V  T  E
A  A  Q     1126
CTAAAGAAAAAGAATCTTTGCAGAAAGATACTGCAGATTCCAGTGCTGCTGCTGCTGCAGAGCA
CTCAGCTCAAG 4050
A  K  E  K  E  S  L  Q  K  D  T  A  D  S  S  A  A  A  A  A  E  H
S  A  Q     1151
TAGGAGACCCAGAAATGAAGAACTTGCCAGACACTAAAGCCATTACACAGAAAGAGGAGATCCA
TAGGAAGAAGA 4125
V  G  D  P  E  M  K  N  L  P  D  T  K  A  I  T  Q  K  E  E  I  H
R  K  K     1176
CAGTTCCCGAGGAAGCCTGGCCAAACAATAAAGAATCCCTACAGATCAATATTGAAGAGTCCGA
ATGTCATTCAG 4200
T  V  P  E  E  A  W  P  N  N  K  E  S  L  Q  I  N  I  E  E  S  E
C  H  S     1201
```

Fig. 6-3 (continuation)

```
AATTTGAAAATACTACCCGTTCTGTCTTCAGGTCAGCAAAGTTTTACATTCATCATCCCGTACA
CCTACCAAGTG 4275
 E   F   E   N   T   T   R   S   V   F   R   S   A   K   F   Y   I   H   H   P   V   H
 L   P   S    1226
ATCAAGATATTTGCCATGAATCTTTGGGAAAGAGTGTTTTCATGAGACATTCTTGGAAAGATTT
CTTTCAGCATC 4350
 D   Q   D   I   C   H   E   S   L   G   K   S   V   F   M   R   H   S   W   K   D   F
 F   Q   H    1251
ATCCAGACAAACATAGAGAACACATGTGTCTTCCTCTTCCTTATCAAAACATGGACAAGACTAA
GACAGATTATA 4425
 H   P   D   K   H   R   E   H   M   C   L   P   L   P   Y   Q   N   M   D   K   T   K
 T   D   Y    1276
CCAGAATAAAGAGCCTCAGCATCAATGTGAATTTGGGAAACAAAGAAGTGATGGATACTACTAA
AAGTCAAGTTA 4500
 T   R   I   K   S   L   S   I   N   V   N   L   G   N   K   E   V   M   D   T   T   K
 S   Q   V    1301
```

Fig. 6-4

```
GAGATTATCCAAAACATAATGGACAAATTAGTGATCCACAAAGGGATCAGAAGGTCACCCCAGA
GCAAACAACTC 4575
R   D   Y   P   K   H   N   G   Q   I   S   D   P   Q   R   D   Q   K   V   T   P   E
Q   T   T   1326
AGCACACTGTGAGTTTGAATGAACTGTGGAACAAGTATCGGGAGCGACAGAGGCAACAGAGACA
GCCTGAGTTGG 4650
Q   H   T   V   S   L   N   E   L   W   N   K   Y   R   E   R   Q   R   Q   Q   R   Q
P   E   L   1351
GTGACAGGAAAGAACTGTCCTTGGTGGACCGACTTGATCGGTTGGCTAAAATTCTTCAGAATCC
AATCACACATT 4725
G   D   R   K   E   L   S   L   V   D   R   L   D   R   L   A   K   I   L   Q   N   P
I   T   H   1376
CTCTCCAGGTCTCAGAAAGTACACATGATGATAGCAGAGGGGAACGAAGTGTGAAGGAATGGAG
TGGTAGACAAC 4800
S   L   Q   V   S   E   S   T   H   D   D   S   R   G   E   R   S   V   K   E   W   S
G   R   Q   1401
AGCAGAGAAATAAGCTTCAGAAAAAGAAGCGGTTTAAAAGCCTAGAGAAAAGCCATAAAAATAC
AGGCGAGCTTA 4875
Q   Q   R   N   K   L   Q   K   K   K   R   F   K   S   L   E   K   S   H   K   N   T
G   E   L   1426
AAAAAAGCAAGGTGCTTTCTCATCATCGAGCTGGGAGGTCTAATCAAATTAAAATTGAACAGAT
TAAATTTGATA 4950
K   K   S   K   V   L   S   H   H   R   A   G   R   S   N   Q   I   K   I   E   Q   I
K   F   D   1451
AATATATTCTGAGTAAACAGCCAGGTTTTAATTATATAAGCAACACTTCTTCGGATTGTCGGCC
CTCAGAGGAGA 5025
K   Y   I   L   S   K   Q   P   G   F   N   Y   I   S   N   T   S   S   D   C   R   P
S   E   E   1476
GTGAGCTGCTCACAGATACTACCACCAACATCCTTTCCGGCACCACTTCTACTGTCGAATCAGA
TATATTGACCC 5100
```

Fig. 6-4 (continuation)

```
S  E  L  L  T  D  T  T  T  N  I  L  S  G  T  T  S  T  V  E  S  D
I  L  T     1501
AAACAGATAGAGAGGTGGCTCTGCACGAAAGGAGTAGCTCTGTTTCCACTATTGACACTGCCCG
GCTGATTCAAG 5175
Q  T  D  R  E  V  A  L  H  E  R  S  S  S  V  S  T  I  D  T  A  R
L  I  Q     1526
CTTTTGGCCATGAAAGAGTATGCTTGTCACCCAGACGAATTAAATTATATAGCAGCATCACCAA
CCAACAGAGGA 5250
A  F  G  H  E  R  V  C  L  S  P  R  R  I  K  L  Y  S  S  I  T  N
Q  Q  R     1551
GATACCTTGAGAAGCGGAGCAAACACAGCAAGAAAGTGCTGAATACAGGTCATCCCCTAGTGAC
TTCTGAGCACA 5325
R  Y  L  E  K  R  S  K  H  S  K  K  V  L  N  T  G  H  P  L  V  T
S  E  H     1576
CCAGAAGGAGACACATCCAGGTAGCAAACCATGTGATTTCTTCTGACTCTATTTCCTCTTCTGC
CAGTAGTTTCC 5400
T  R  R  R  H  I  Q  V  A  N  H  V  I  S  S  D  S  I  S  S  S  A
S  S  F     1601
TGAGCTCAAACTCTACTTTTTGCAACAAGCAGAATGTACACATGTTAAACAAGGGCATACAAGC
AGGTAACTTGG 5475
L  S  S  N  S  T  F  C  N  K  Q  N  V  H  M  L  N  K  G  I  Q  A
G  N  L     1626
AGATTGTGAACGGTGCCAAAAAACACACTCGAGATGTTGGGATAACTTTCCCAACTCCAAGTTC
CAGCGAGGCTA 5550
E  I  V  N  G  A  K  K  H  T  R  D  V  G  I  T  F  P  T  P  S  S
S  E  A     1651
AATTGGAAGAGAACAGTGATGTGACTTCTTGGTCAGAAGAAAAACGTGAAGAGAAAATGCTCTT
TACCGGTTATC 5625
K  L  E  E  N  S  D  V  T  S  W  S  E  E  K  R  E  E  K  M  L  F
T  G  Y     1676
```

Fig. 6-4 (continuation)

```
CTGAGGACAGAAAGTTAAAAAAGAACAAGAAGAATTCCCATGAAGGAGTTTCCTGGTTTGTTCC
TGTGGAAAATG  5700
 P   E   D   R   K   L   K   K   N   K   K   N   S   H   E   G   V   S   W   F   V   P
 V   E   N  1701
TGGAGTCTAGATCAAAGAAGGAAAACGTGCCTAACACTTGTGGCCCTGGCATCTCCTGGTTTGA
ACCAATAACCA  5775
 V   E   S   R   S   K   K   E   N   V   P   N   T   C   G   P   G   I   S   W   F   E
 P   I   T  1726
AGACCAGACCCTGGAGGGAGCCACTGCGGGAGCAGAACTGTCAGGGGCAGCACCTGGACGGTCG
GGGCTACCTGG  5850
 K   T   R   P   W   R   E   P   L   R   E   Q   N   C   Q   G   Q   H   L   D   G   R
 G   Y   L  1751
CAGGCCCAGGCAGAGAGGCTGGCAGAGACCTACTGAAGCCATTTGTGAGAGCAACCCTTCAGGA
ATCGCTTCAGT  5925
 A   G   P   G   R   E   A   G   R   D   L   L   K   P   F   V   R   A   T   L   Q   E
 S   L   Q  1776
```

Fig. 6-5

```
TTCACAGACCTGACTTCATCTCCCGCTCTGGGGAGCGGATAAAGCGCCTGAAGTTAATAGTCCA
GGAGAGGAAGC 6000
 F   H   R   P   D   F   I   S   R   S   G   E   R   I   K   R   L   K   L   I   V   Q
 E   R   K   1801
TGCAGAGCATGTTACAGACCGAGCGGGATGCACTATTCAACATTGACAGGGAACGGCAGGGCCA
CCAGAATCGCA 6075
 L   Q   S   M   L   Q   T   E   R   D   A   L   F   N   I   D   R   E   R   Q   G   H
 Q   N   R   1826
TGTGCCCGCTGCCCAAGAGAGTCTTCCTGGCTATCCAGAAGAACAAGCCTATCAGCAAGAAGGA
AATGATTCAGA 6150
 M   C   P   L   P   K   R   V   F   L   A   I   Q   K   N   K   P   I   S   K   K   E
 M   I   Q   1851
GGTCCAAACGGATTTATGAGCAGCTTCCAGAAGTACAGAAAAAGAGAGAAGAAGAGAAGAGAAA
ATCAGAATATA 6225
 R   S   K   R   I   Y   E   Q   L   P   E   V   Q   K   K   R   E   E   E   K   R   K
 S   E   Y   1876
AGTCATACCGGCTGCGAGCCCAGCTATATAAAAAGAGAGTGACCAATCAACTTCTGGGGAGAAA
AGTTCCCTGGG 6300
 K   S   Y   R   L   R   A   Q   L   Y   K   K   R   V   T   N   Q   L   L   G   R   K
 V   P   W   1901
ACTGAcacaagtttattttcctcagagccttggaattctattttatgaacctagagaagcagaa
tccttacttttt 6375
 d   *
 1902
gtgagtctggttgaataaagcttattctttgtccatgtgtatttagaaatagtaacttctaaa
gagtctggaac 6450
aaagtggtgattaaaattcctaatggtttgggagcaatactttctgcatagtggccttgtccaa
tggcctgtgtg 6525
ttacaatgatatgatcatttctcaagaataagtcccttttttgtatgtgttttatactttaga
aataaaaact 6600
```

Fig. 6-5 (Continuation)

ttagattaactc

6612

Fig. 7 ALMS1 splice junctions

| Exon | Exon size (bp) | 5' splice donor | 3'splice acceptor | Intron size (kb) |
|---|---|---|---|---|
| 1 | 742 | ACGAGCACATGgtaagaaga....agaggtcGGACCTTATA | | 1.096 |
| 2 | 134 | TTGTCCAAGgtataaaaga......atcttctagGGTTTACAGAG | | 34.342 |
| 3 | 1865 | TGCAGATCGgtgagtctcat.....ttggtcagATTACCAGAGA | | >24.5 |
| 4 | 242 | CACAGATGgtaagagaat.......cctccttagGCCAGCCTTT | | >21.6 |
| 5 | 126 | CCATTCAGgtattatg..........ttttctgtagGATCCAATGA | | 15.323 |
| 6 | 171 | AAAATGCAGgtaactggat.....gttattccagATGCCTCAGTTC | | 6.786 |
| 7 | 135 | ATACTGCAGgtagctaaact......cctttcgtagATTCCAGTGC | | 1.618 |
| 8 | 171 | ATATTGAAGgtaatgggat.........ctccttttcagAGTCCGAATGTC | | 13.130 |
| 9 | 1163 | ACACATCCAGgtacatggcta....tatttttctagGTAGCAAACCAT | | >25.6 |
| 10 | 121 | TACAAGCAGgtaattacttg......ccttcccctcagGTAACTTGGAGAT | | 1.158 |
| 11 | 204 | CCCATGAAGgtcagtttctcat.....tttcctgtagGAGTTTCCTGGT | | 0.315 |
| 12 | 242 | ACCCTTCAGgtgcagtgacgt....ttttcttttagGAATCGCTTCAGT | | 0.750 |
| 13 | 184 | CCAAGAGAGgtacgccctgccc....tcttgcctagTCTTCCTGGCTAT | | 0.874 |
| 14 | 64 | GGTCCAAACGgtaagaccaaga....gagatctcatGACTCTGCACCC | | >6.144 |
| 15 | 100 | TATAAAAAGgtcagtgggtc......cttctacagAGAGTGACCAAT | | 0.998 |
| 16 | 45 | CCCTGGGACTGA...3'UTR | | |

Fig. 8 Primer pairs for ALMS1 mutation analysis

| Primer Pair | Size | Exon |
|---|---|---|
| 5'- TGCAGGTTTTAGAGATGTTGG-3'<br>5'- TGCTTGTATTTTTCATTGGCT-3' | 929 bp | 1 |
| 5'- CATACTAAGCATTGCAGTGGG-3'<br>5'- GAATGGGTGATGGAATTAGGA-3' | 312 bp | 2 |
| 5'- TGGTCTAATCTTAGCGTGGGT-3'<br>5'- CCGTGTGATTTCTCTGAGTGG-3' | 2081 bp | 3 |
| 5'- TTGACATTGATGTGTCCACAAT-3'<br>5'- ATTTGCATAGCTGTCAACAGAA-3' | 533 bp | 4 |
| 5'- GCCTGAAACATAGAAGGCATT-3'<br>5'- GGAGTGACAAAAGTCCAGTGC-3' | 301 bp | 5 |
| 5'- CTCAATCTCATGTCGCTATTTG-3'<br>5'- TGCTCAATATAACAGCAAGGAG-3' | 355 bp | 6 |
| 5'- GGGTTTTGTTTGTAATTGTGG-3'<br>5'- GAGAGCTGAAGACAGCAAGAAG-3' | 343 bp | 7 |
| 5'- CGCTACCTCTTTTTCTGACTG-3'<br>5'- TGGAAACACTAACACTGACCCT-3' | 457 bp | 8 |
| 5'- GAGGCTACTAAGCAACAAGGC-3'<br>5'- GCAGTCACATTGCCAGATG-3' | 1376 bp | 9 |
| 5'- TGGCTTGCTTATCCTGTGG-3'<br>5'- TCTGACAAGATGAAAATTGGC-3' | 330 bp | 10 |
| 5'- TCCCAGAGACACCTATGATCC-3'<br>5'- CTTGGAGTTGGGAAAGTTATC-3' | 101 bp | 11 |
| 5'- GCCAAAAAACACACTCGAGATGTTG-3'<br>5'- CCAAGTCACAGAGCCAGCTT-3 | 818 bp | 11 |
| 5'- GCATATCCTGGATAAGAGCTG-3'<br>5'- GAGAAACCCAACCCTCGTG-3' | 484 bp | 12 |
| 5'- TCAGACTTCCCCAAACCTCT-3'<br>5'- TCAGTGCCATAAGTGAGAAATG-3' | 1379 bp | 13,14 |
| 5'- GACTCTGCACCCTGGTAACC-3'<br>5'- CGCCAATAAACCTGATCCAT-3' | 205 bp | 15 |
| 5'- GCCTCTGATGGCAGTAATATCT-3'<br>5'- TCTCCAGATGGGAAAGAATTG-3' | 435 bp | 16 |

SEQUENCE LISTING

```
<160> NUMBER OF SEQ ID NOS: 34

<210> SEQ ID NO 1
<211> LENGTH: 6612
<212> TYPE: DNA
<213> ORGANISM: Homo sapiens
<220> FEATURE:
<221> NAME/KEY: CDS
<222> LOCATION: (597)..(6302)
<223> OTHER INFORMATION:

<400> SEQUENCE: 1
agtaaaggta ttctaaagat ttcagctgtc cctgaactaa ctgatgtgaa tactggaaaa        60
ccagtatctc tctctagttc ttattttcac agagagaaat cgaatatttt cagtccacag       120
gaattgccag gtagtcatgt aactgaagat gtgctgaagg tttcaacaat tcctggacca       180
gctggccaga aaacagtatt accaacagct cttcctagtt cctttcaca tcgagagaaa        240 ccagatattt tctatcaaaa ggatttgcca gatagacatc taactgaaga tgctctaaag       300
atctcaagtg ctcttgggca agctgatcaa attaccggat tacaaacagt tccctctggt       360
acttactcac atggtgagaa tcacaagctt gtttcagaac atgtccaaag gctaatagat       420
atttgaattc ttctgactcc agtgttagct caaataatgt gcttttaaat tctcaggctg       480
atgacagagt tgtaataaat aaaccagaat ctgcaggttt tagagatgtt ggctctgaag       540
aaatccagga tgcagaaaat agtgctaaaa ctcttaagga aattcggaca cttttg atg      599
                                                                   Met
                                                                    1 gag gca gaa aat atg gca ctg aaa cga tgc aat ttt cct gct ccc ctt        647
Glu Ala Glu Asn Met Ala Leu Lys Arg Cys Asn Phe Pro Ala Pro Leu
        5                  10                   15 gcc cgt ttc aga gat att agt gat att tca ttt ata caa tct aag aag        695
Ala Arg Phe Arg Asp Ile Ser Asp Ile Ser Phe Ile Gln Ser Lys Lys
     20                  25                  30 gtg gtt tgc ttc aaa gaa ccc tct tcc acg ggt gta tct aat ggt gat        743
Val Val Cys Phe Lys Glu Pro Ser Ser Thr Gly Val Ser Asn Gly Asp
 35                  40                  45 ttg ctt cac aga cag cca ttc aca gag gaa agc cca agc agc agg tgc        791
Leu Leu His Arg Gln Pro Phe Thr Glu Glu Ser Pro Ser Ser Arg Cys
50                  55                  60                  65 ata cag aag gat att ggc aca cag acg aat ttg aaa tgc cgg aga ggc        839
Ile Gln Lys Asp Ile Gly Thr Gln Thr Asn Leu Lys Cys Arg Arg Gly
                 70                  75                  80 att gaa aat tgg gag ttt att agt tca act aca gtt aga agt cct cta        887
Ile Glu Asn Trp Glu Phe Ile Ser Ser Thr Thr Val Arg Ser Pro Leu
             85                  90                  95
```

-continued

| | | |
|---|---|---|
| cag gaa gca gag agc aaa gtc agt atg gca tta gaa gaa act ctt agg<br>Gln Glu Ala Glu Ser Lys Val Ser Met Ala Leu Glu Glu Thr Leu Arg<br>    100                 105                 110 | 935 | |
| caa tat caa gca gcc aaa tct gta atg agg tct gaa cct gaa ggg tgt<br>Gln Tyr Gln Ala Ala Lys Ser Val Met Arg Ser Glu Pro Glu Gly Cys<br>115                 120                 125 | 983 | |
| agt gga acc att ggg aat aaa att att atc cct atg atg act gtc ata<br>Ser Gly Thr Ile Gly Asn Lys Ile Ile Ile Pro Met Met Thr Val Ile<br>130                 135                 140             145 | 1031 | |
| aaa agt gat tca agt agt gat gcc agt gat gga aat ggt tcc tgc tcg<br>Lys Ser Asp Ser Ser Asp Ala Ser Asp Gly Asn Gly Ser Cys Ser<br>            150                 155                 160 | 1079 | |
| tgg gac agt aat tta cca gag tct ttg gaa tca gtt tct gat gtt ctt<br>Trp Asp Ser Asn Leu Pro Glu Ser Leu Glu Ser Val Ser Asp Val Leu<br>            165                 170                 175 | 1127 | |
| cta aac ttc ttt cca tat gtt tca ccc aag aca agt ata aca gat agc<br>Leu Asn Phe Phe Pro Tyr Val Ser Pro Lys Thr Ser Ile Thr Asp Ser<br>            180                 185                 190 | 1175 | |
| agg gag gaa gag ggt gtg tca gag agt gag gat ggt ggt ggt agc agt<br>Arg Glu Glu Glu Gly Val Ser Glu Ser Glu Asp Gly Gly Gly Ser Ser<br>195                 200                 205 | 1223 | |
| gta gat tca ctg gct gca cat gtg aaa aac ctt ctg caa tgt gaa tcc<br>Val Asp Ser Leu Ala Ala His Val Lys Asn Leu Leu Gln Cys Glu Ser<br>210                 215                 220             225 | 1271 | |
| tca ctg aat cat gct aaa gaa ata ctc aga aat gca gag gag gag gaa<br>Ser Leu Asn His Ala Lys Glu Ile Leu Arg Asn Ala Glu Glu Glu Glu<br>            230                 235                 240 | 1319 | |
| agc cgg gta cga gca cat gcc tgg aat atg aag ttc aat tta gca cat<br>Ser Arg Val Arg Ala His Ala Trp Asn Met Lys Phe Asn Leu Ala His<br>            245                 250                 255 | 1367 | |
| gat tgt gga tac tcc att tca gaa tta aat gaa gat gac agg agg aaa<br>Asp Cys Gly Tyr Ser Ile Ser Glu Leu Asn Glu Asp Asp Arg Arg Lys<br>            260                 265                 270 | 1415 | |
| gta gaa gag atc aag gca gag tta ttt ggt cat gga aga aca act gac<br>Val Glu Glu Ile Lys Ala Glu Leu Phe Gly His Gly Arg Thr Thr Asp<br>275                 280                 285 | 1463 | |
| ttg tcc aag ggt tta cag agt cca cgg gga atg gga tgc aag cca gaa<br>Leu Ser Lys Gly Leu Gln Ser Pro Arg Gly Met Gly Cys Lys Pro Glu<br>290                 295                 300             305 | 1511 | |
| gct gta tgt agt cac att att att gag agc cat gaa aag gga tgt ttc<br>Ala Val Cys Ser His Ile Ile Ile Glu Ser His Glu Lys Gly Cys Phe<br>            310                 315                 320 | 1559 | |
| cgg act cta act tct gaa cat cca caa cta gat aga cac cct tgt gct<br>Arg Thr Leu Thr Ser Glu His Pro Gln Leu Asp Arg His Pro Cys Ala<br>            325                 330                 335 | 1607 | |
| ttc aga tct gct gga ccc tca gaa atg acc aga gga cgg cag aac cca<br>Phe Arg Ser Ala Gly Pro Ser Glu Met Thr Arg Gly Arg Gln Asn Pro<br>            340                 345                 350 | 1655 | |
| tca tca tgc aga gcc aag cat gtc aac ctt tct gca tcc tta gac cag<br>Ser Ser Cys Arg Ala Lys His Val Asn Leu Ser Ala Ser Leu Asp Gln<br>355                 360                 365 | 1703 | |
| aac aac tcc cat ttc aaa gtt tgg aat tcc ttg cag tta aaa agt cat<br>Asn Asn Ser His Phe Lys Val Trp Asn Ser Leu Gln Leu Lys Ser His<br>370                 375                 380             385 | 1751 | |
| tcc cca ttt cag aac ttt ata cct gat gaa ttc aaa atc agc aaa ggt<br>Ser Pro Phe Gln Asn Phe Ile Pro Asp Glu Phe Lys Ile Ser Lys Gly<br>            390                 395                 400 | 1799 | |
| ctt cga atg cca ttc gat gaa aag atg gac cct tgg ctg tca gaa tta<br>Leu Arg Met Pro Phe Asp Glu Lys Met Asp Pro Trp Leu Ser Glu Leu<br>            405                 410                 415 | 1847 | |

-continued

| | | |
|---|---|---|
| gta gaa cct gct ttt gtg cca cct aaa gaa gtg gat ttt cat tct tca<br>Val Glu Pro Ala Phe Val Pro Pro Lys Glu Val Asp Phe His Ser Ser<br>420                                425                              430 | 1895 | |
| tca caa atg ccg tcc cca gaa ccc atg aaa aag ttt act acc tcc atc<br>Ser Gln Met Pro Ser Pro Glu Pro Met Lys Lys Phe Thr Thr Ser Ile<br>435                                440                              445 | 1943 | |
| act ttt tca tct cac cga cat tct aaa tgc att tcc aat tcc tct gtt<br>Thr Phe Ser Ser His Arg His Ser Lys Cys Ile Ser Asn Ser Ser Val<br>450                                455                              460                             465 | 1991 | |
| gtt aag gtt ggt gtt act gaa ggt agc cag tgt act gga gca tct gtg<br>Val Lys Val Gly Val Thr Glu Gly Ser Gln Cys Thr Gly Ala Ser Val<br>                 470                              475                              480 | 2039 | |
| ggg gta ttt aat tct cat ttc act gaa gaa caa aat cct ccc aga gat<br>Gly Val Phe Asn Ser His Phe Thr Glu Glu Gln Asn Pro Pro Arg Asp<br>485                               490                              495 | 2087 | |
| ctt aaa cag aaa acc tct tcc cct tca tca ttt aaa atg cat agt aat<br>Leu Lys Gln Lys Thr Ser Ser Pro Ser Ser Phe Lys Met His Ser Asn<br>500                                505                             510 | 2135 | |
| tca caa gat aaa gaa gtg act att tta gca gaa ggt aga agg caa agc<br>Ser Gln Asp Lys Glu Val Thr Ile Leu Ala Glu Gly Arg Arg Gln Ser<br>515                                520                             525 | 2183 | |
| caa aaa tta cct gtt gat ttt gag cgt tct ttt caa gaa gaa aaa ccc<br>Gln Lys Leu Pro Val Asp Phe Glu Arg Ser Phe Gln Glu Glu Lys Pro<br>530                                535                             540                             545 | 2231 | |
| tta gaa aga tca gat ttt aca ggc agt cat tct gag ccc agt acc agg<br>Leu Glu Arg Ser Asp Phe Thr Gly Ser His Ser Glu Pro Ser Thr Arg<br>                 550                              555                              560 | 2279 | |
| gca aat tgt agc aat ttc aag gaa att cag att tct gat aac cat acc<br>Ala Asn Cys Ser Asn Phe Lys Glu Ile Gln Ile Ser Asp Asn His Thr<br>565                                570                             575 | 2327 | |
| ctt att agc atg ggc aga cca agt tcc acc cta gga gta aac aga tcg<br>Leu Ile Ser Met Gly Arg Pro Ser Ser Thr Leu Gly Val Asn Arg Ser<br>580                                585                             590 | 2375 | |
| agt tcc aga cta gga gta aaa gag aag aat gta act ata act cca gat<br>Ser Ser Arg Leu Gly Val Lys Glu Lys Asn Val Thr Ile Thr Pro Asp<br>595                                600                             605 | 2423 | |
| ctt cct tct tgc att ttt ctt gaa caa cga gag ctc ttt gaa caa agc<br>Leu Pro Ser Cys Ile Phe Leu Glu Gln Arg Glu Leu Phe Glu Gln Ser<br>610                                615                             620                             625 | 2471 | |
| aaa gcc cca cgt gca gat gac cat gtg agg aaa cac cat tct ccc tct<br>Lys Ala Pro Arg Ala Asp Asp His Val Arg Lys His His Ser Pro Ser<br>                 630                              635                              640 | 2519 | |
| cct caa cat cag gat tat gta gct cca gac ctt cct tct tgc att ttt<br>Pro Gln His Gln Asp Tyr Val Ala Pro Asp Leu Pro Ser Cys Ile Phe<br>645                                650                             655 | 2567 | |
| ctt gaa caa cga gaa ctc ttt gaa cag tgc aaa gcc cca tat gta gat<br>Leu Glu Gln Arg Glu Leu Phe Glu Gln Cys Lys Ala Pro Tyr Val Asp<br>                 660                              665                              670 | 2615 | |
| cat caa atg aga gaa aac cat tct ccc ctt cct caa ggt cag gat tct<br>His Gln Met Arg Glu Asn His Ser Pro Leu Pro Gln Gly Gln Asp Ser<br>675                                680                             685 | 2663 | |
| ata gct tca gac ctt ccg tct ccc att tct ctt gaa caa tgc caa agc<br>Ile Ala Ser Asp Leu Pro Ser Pro Ile Ser Leu Glu Gln Cys Gln Ser<br>690                                695                             700                             705 | 2711 | |
| aaa gcg cca ggt gta gat gac caa atg aat aaa cac cat ttt ccc ctt<br>Lys Ala Pro Gly Val Asp Asp Gln Met Asn Lys His His Phe Pro Leu<br>                 710                              715                              720 | 2759 | |
| cct caa ggt cag gat tgt gta gtg gaa aag aat aat caa cat aag cct<br>Pro Gln Gly Gln Asp Cys Val Val Glu Lys Asn Asn Gln His Lys Pro | 2807 | |

-continued

| | | |
|---|---|---|
| aaa tca cac att tct aat ata aat gtt gaa gcc aag ttc aat act gtg<br>Lys Ser His Ile Ser Asn Ile Asn Val Glu Ala Lys Phe Asn Thr Val<br>        740                        745                          750 | 2855 |
| gtc tcc cag tca gcc cca aat cac tgt aca tta gca gca tct gca tct<br>Val Ser Gln Ser Ala Pro Asn His Cys Thr Leu Ala Ala Ser Ala Ser<br>    755                        760                          765 | 2903 |
| act cct cct tca aat aga aaa gca ctt tct tgt gtt cat ata act ctt<br>Thr Pro Pro Ser Asn Arg Lys Ala Leu Ser Cys Val His Ile Thr Leu<br>770                        775                        780                        785 | 2951 |
| tgt ccc aag act tct tcc aag ttg gat agt gga act tta gat gaa aga<br>Cys Pro Lys Thr Ser Ser Lys Leu Asp Ser Gly Thr Leu Asp Glu Arg<br>        790                        795                        800 | 2999 |
| ttc cat tca ttg gat gct gct tct aaa gcg agg atg aat agt gag ttt<br>Phe His Ser Leu Asp Ala Ala Ser Lys Ala Arg Met Asn Ser Glu Phe<br>            805                      810                        815 | 3047 |
| aac ttt gac tta cat act gta tct tcg aga tca ctg gaa cca acc tcc<br>Asn Phe Asp Leu His Thr Val Ser Ser Arg Ser Leu Glu Pro Thr Ser<br>                820                      825                        830 | 3095 |
| aaa tta ttg acc agt aaa cct gta gca cag gat caa gaa tct tta ggt<br>Lys Leu Leu Thr Ser Lys Pro Val Ala Gln Asp Gln Glu Ser Leu Gly<br>835                        840                        845 | 3143 |
| ttt cta gga cct aaa tct tca ctg gat ttc caa gtc gta cag cct tct<br>Phe Leu Gly Pro Lys Ser Ser Leu Asp Phe Gln Val Val Gln Pro Ser<br>850                        855                        860                        865 | 3191 |
| ctt cca gac agt aac act att act cag gac ttg aaa acc ata cct tct<br>Leu Pro Asp Ser Asn Thr Ile Thr Gln Asp Leu Lys Thr Ile Pro Ser<br>        870                        875                        880 | 3239 |
| cag aat agc cag ata gta acc tcc agg caa ata caa gtg aac att tca<br>Gln Asn Ser Gln Ile Val Thr Ser Arg Gln Ile Gln Val Asn Ile Ser<br>            885                      890                        895 | 3287 |
| gat ttc gaa gga cat tcc aat cca gag ggg acc cca gta ttt gca gat<br>Asp Phe Glu Gly His Ser Asn Pro Glu Gly Thr Pro Val Phe Ala Asp<br>        900                        905                        910 | 3335 |
| cga tta cca gag aag atg aag acc cca ctt tct gct ttc tct gaa aaa<br>Arg Leu Pro Glu Lys Met Lys Thr Pro Leu Ser Ala Phe Ser Glu Lys<br>915                        920                        925 | 3383 |
| ttg tca tct gat gca gtc act cag ata aca aca gaa agt cca gaa aag<br>Leu Ser Ser Asp Ala Val Thr Gln Ile Thr Thr Glu Ser Pro Glu Lys<br>930                        935                        940                        945 | 3431 |
| acc cta ttt tca tct gag att ttt att aat gct gaa gat cgt gga cat<br>Thr Leu Phe Ser Ser Glu Ile Phe Ile Asn Ala Glu Asp Arg Gly His<br>            950                      955                        960 | 3479 |
| gaa att ata gag cct ggt aac cag aag cta cgc aaa gct cct gtc aag<br>Glu Ile Ile Glu Pro Gly Asn Gln Lys Leu Arg Lys Ala Pro Val Lys<br>            965                      970                        975 | 3527 |
| ttt gcc tca tca tct tca gtc caa cag gtt act ttt tct cgc ggc aca<br>Phe Ala Ser Ser Ser Ser Val Gln Gln Val Thr Phe Ser Arg Gly Thr<br>            980                      985                        990 | 3575 |
| gat ggc cag cct tta tta ttg cca tat aag cct tct ggt agt acc aag<br>Asp Gly Gln Pro Leu Leu Leu Pro Tyr Lys Pro Ser Gly Ser Thr Lys<br>    995                        1000                      1005 | 3623 |
| atg tat tat gtt cca caa tta aga caa att cct cca tct ccg gat<br>Met Tyr Tyr Val Pro Gln Leu Arg Gln Ile Pro Pro Ser Pro Asp<br>1010                          1015                      1020 | 3668 |
| tcc aaa tca gat acc acc gtt gaa agc tcc cat tca gga tcc aat<br>Ser Lys Ser Asp Thr Thr Val Glu Ser Ser His Ser Gly Ser Asn<br>1025                        1030                      1035 | 3713 |
| gat gcc att gct cca gac ttc cca gct cag gtg cta ggc aca aga | 3758 |

-continued

| | | | | | | | | | | |
|---|---|---|---|---|---|---|---|---|---|---|
| Asp | Ala | Ile | Ala | Pro | Asp | Phe | Pro | Ala | Gln | Val | Leu | Gly | Thr | Arg |
| 1040 | | | | 1045 | | | | | 1050 | | | | | |

| gat | gat | gac | ctc | tca | gcc | act | gtt | aac | att | aaa | cat | aaa | gaa | gga | 3803 |
| Asp | Asp | Asp | Leu | Ser | Ala | Thr | Val | Asn | Ile | Lys | His | Lys | Glu | Gly | |
| 1055 | | | | 1060 | | | | | 1065 | | | | | | |

| atc | tac | agt | aag | agg | gta | gtg | act | aag | gca | tcc | ttg | cca | gtg | gga | 3848 |
| Ile | Tyr | Ser | Lys | Arg | Val | Val | Thr | Lys | Ala | Ser | Leu | Pro | Val | Gly | |
| 1070 | | | | 1075 | | | | | 1080 | | | | | | |

| gaa | aaa | ccc | ttg | cag | aat | gaa | aat | gca | gat | gcc | tca | gtt | caa | gtg | 3893 |
| Glu | Lys | Pro | Leu | Gln | Asn | Glu | Asn | Ala | Asp | Ala | Ser | Val | Gln | Val | |
| 1085 | | | | 1090 | | | | | 1095 | | | | | | |

| cta | atc | act | ggg | gat | gag | aac | ctc | tca | gac | aaa | aaa | cag | caa | gag | 3938 |
| Leu | Ile | Thr | Gly | Asp | Glu | Asn | Leu | Ser | Asp | Lys | Lys | Gln | Gln | Glu | |
| 1100 | | | | 1105 | | | | | 1110 | | | | | | |

| att | cac | agt | aca | agg | gca | gtg | act | gag | gct | gcc | cag | gct | aaa | gaa | 3983 |
| Ile | His | Ser | Thr | Arg | Ala | Val | Thr | Glu | Ala | Ala | Gln | Ala | Lys | Glu | |
| 1115 | | | | 1120 | | | | | 1125 | | | | | | |

| aaa | gaa | tct | ttg | cag | aaa | gat | act | gca | gat | tcc | agt | gct | gct | gct | 4028 |
| Lys | Glu | Ser | Leu | Gln | Lys | Asp | Thr | Ala | Asp | Ser | Ser | Ala | Ala | Ala | |
| 1130 | | | | 1135 | | | | | 1140 | | | | | | |

| gct | gca | gag | cac | tca | gct | caa | gta | gga | gac | cca | gaa | atg | aag | aac | 4073 |
| Ala | Ala | Glu | His | Ser | Ala | Gln | Val | Gly | Asp | Pro | Glu | Met | Lys | Asn | |
| 1145 | | | | 1150 | | | | | 1155 | | | | | | |

| ttg | cca | gac | act | aaa | gcc | att | aca | cag | aaa | gag | gag | atc | cat | agg | 4118 |
| Leu | Pro | Asp | Thr | Lys | Ala | Ile | Thr | Gln | Lys | Glu | Glu | Ile | His | Arg | |
| 1160 | | | | 1165 | | | | | 1170 | | | | | | |

| aag | aag | aca | gtt | ccc | gag | gaa | gcc | tgg | cca | aac | aat | aaa | gaa | tcc | 4163 |
| Lys | Lys | Thr | Val | Pro | Glu | Glu | Ala | Trp | Pro | Asn | Asn | Lys | Glu | Ser | |
| 1175 | | | | 1180 | | | | | 1185 | | | | | | |

| cta | cag | atc | aat | att | gaa | gag | tcc | gaa | tgt | cat | tca | gaa | ttt | gaa | 4208 |
| Leu | Gln | Ile | Asn | Ile | Glu | Glu | Ser | Glu | Cys | His | Ser | Glu | Phe | Glu | |
| 1190 | | | | 1195 | | | | | 1200 | | | | | | |

| aat | act | acc | cgt | tct | gtc | ttc | agg | tca | gca | aag | ttt | tac | att | cat | 4253 |
| Asn | Thr | Thr | Arg | Ser | Val | Phe | Arg | Ser | Ala | Lys | Phe | Tyr | Ile | His | |
| 1205 | | | | 1210 | | | | | 1215 | | | | | | |

| cat | ccc | gta | cac | cta | cca | agt | gat | caa | gat | att | tgc | cat | gaa | tct | 4298 |
| His | Pro | Val | His | Leu | Pro | Ser | Asp | Gln | Asp | Ile | Cys | His | Glu | Ser | |
| 1220 | | | | 1225 | | | | | 1230 | | | | | | |

| ttg | gga | aag | agt | gtt | ttc | atg | aga | cat | tct | tgg | aaa | gat | ttc | ttt | 4343 |
| Leu | Gly | Lys | Ser | Val | Phe | Met | Arg | His | Ser | Trp | Lys | Asp | Phe | Phe | |
| 1235 | | | | 1240 | | | | | 1245 | | | | | | |

| cag | cat | cat | cca | gac | aaa | cat | aga | gaa | cac | atg | tgt | ctt | cct | ctt | 4388 |
| Gln | His | His | Pro | Asp | Lys | His | Arg | Glu | His | Met | Cys | Leu | Pro | Leu | |
| 1250 | | | | 1255 | | | | | 1260 | | | | | | |

| cct | tat | caa | aac | atg | gac | aag | act | aag | aca | gat | tat | acc | aga | ata | 4433 |
| Pro | Tyr | Gln | Asn | Met | Asp | Lys | Thr | Lys | Thr | Asp | Tyr | Thr | Arg | Ile | |
| 1265 | | | | 1270 | | | | | 1275 | | | | | | |

| aag | agc | ctc | agc | atc | aat | gtg | aat | ttg | gga | aac | aaa | gaa | gtg | atg | 4478 |
| Lys | Ser | Leu | Ser | Ile | Asn | Val | Asn | Leu | Gly | Asn | Lys | Glu | Val | Met | |
| 1280 | | | | 1285 | | | | | 1290 | | | | | | |

| gat | act | act | aaa | agt | caa | gtt | aga | gat | tat | cca | aaa | cat | aat | gga | 4523 |
| Asp | Thr | Thr | Lys | Ser | Gln | Val | Arg | Asp | Tyr | Pro | Lys | His | Asn | Gly | |
| 1295 | | | | 1300 | | | | | 1305 | | | | | | |

| caa | att | agt | gat | cca | caa | agg | gat | cag | aag | gtc | acc | cca | gag | caa | 4568 |
| Gln | Ile | Ser | Asp | Pro | Gln | Arg | Asp | Gln | Lys | Val | Thr | Pro | Glu | Gln | |
| 1310 | | | | 1315 | | | | | 1320 | | | | | | |

| aca | act | cag | cac | act | gtg | agt | ttg | aat | gaa | ctg | tgg | aac | aag | tat | 4613 |
| Thr | Thr | Gln | His | Thr | Val | Ser | Leu | Asn | Glu | Leu | Trp | Asn | Lys | Tyr | |
| 1325 | | | | 1330 | | | | | 1335 | | | | | | |

|     |     |     |     |     |     |     |     |     |     |     |     |     |     |     |      |
| --- | --- | --- | --- | --- | --- | --- | --- | --- | --- | --- | --- | --- | --- | --- | ---- |
| cgg | gag | cga | cag | agg | caa | cag | aga | cag | cct | gag | ttg | ggt | gac | agg | 4658 |
| Arg | Glu | Arg | Gln | Arg | Gln | Gln | Arg | Gln | Pro | Glu | Leu | Gly | Asp | Arg |      |
| 1340 |    |    |    | 1345 |   |    |    |    | 1350 |   |    |    |    |    |      |
| aaa | gaa | ctg | tcc | ttg | gtg | gac | cga | ctt | gat | cgg | ttg | gct | aaa | att | 4703 |
| Lys | Glu | Leu | Ser | Leu | Val | Asp | Arg | Leu | Asp | Arg | Leu | Ala | Lys | Ile |      |
| 1355 |    |    |    | 1360 |   |    |    |    | 1365 |   |    |    |    |    |      |
| ctt | cag | aat | cca | atc | aca | cat | tct | ctc | cag | gtc | tca | gaa | agt | aca | 4748 |
| Leu | Gln | Asn | Pro | Ile | Thr | His | Ser | Leu | Gln | Val | Ser | Glu | Ser | Thr |      |
| 1370 |    |    |    | 1375 |   |    |    |    | 1380 |   |    |    |    |    |      |
| cat | gat | gat | agc | aga | ggg | gaa | cga | agt | gtg | aag | gaa | tgg | agt | ggt | 4793 |
| His | Asp | Asp | Ser | Arg | Gly | Glu | Arg | Ser | Val | Lys | Glu | Trp | Ser | Gly |      |
| 1385 |    |    |    | 1390 |   |    |    |    | 1395 |   |    |    |    |    |      |
| aga | caa | cag | cag | aga | aat | aag | ctt | cag | aaa | aag | aag | cgg | ttt | aaa | 4838 |
| Arg | Gln | Gln | Gln | Arg | Asn | Lys | Leu | Gln | Lys | Lys | Lys | Arg | Phe | Lys |      |
| 1400 |    |    |    | 1405 |   |    |    |    | 1410 |   |    |    |    |    |      |
| agc | cta | gag | aaa | agc | cat | aaa | aat | aca | ggc | gag | ctt | aaa | aaa | agc | 4883 |
| Ser | Leu | Glu | Lys | Ser | His | Lys | Asn | Thr | Gly | Glu | Leu | Lys | Lys | Ser |      |
| 1415 |    |    |    | 1420 |   |    |    |    | 1425 |   |    |    |    |    |      |
| aag | gtg | ctt | tct | cat | cat | cga | gct | ggg | agg | tct | aat | caa | att | aaa | 4928 |
| Lys | Val | Leu | Ser | His | His | Arg | Ala | Gly | Arg | Ser | Asn | Gln | Ile | Lys |      |
| 1430 |    |    |    | 1435 |   |    |    |    | 1440 |   |    |    |    |    |      |
| att | gaa | cag | att | aaa | ttt | gat | aaa | tat | att | ctg | agt | aaa | cag | cca | 4973 |
| Ile | Glu | Gln | Ile | Lys | Phe | Asp | Lys | Tyr | Ile | Leu | Ser | Lys | Gln | Pro |      |
| 1445 |    |    |    | 1450 |   |    |    |    | 1455 |   |    |    |    |    |      |
| ggt | ttt | aat | tat | ata | agc | aac | act | tct | tcg | gat | tgt | cgg | ccc | tca | 5018 |
| Gly | Phe | Asn | Tyr | Ile | Ser | Asn | Thr | Ser | Ser | Asp | Cys | Arg | Pro | Ser |      |
| 1460 |    |    |    | 1465 |   |    |    |    | 1470 |   |    |    |    |    |      |
| gag | gag | agt | gag | ctg | ctc | aca | gat | act | acc | acc | aac | atc | ctt | tcc | 5063 |
| Glu | Glu | Ser | Glu | Leu | Leu | Thr | Asp | Thr | Thr | Thr | Asn | Ile | Leu | Ser |      |
| 1475 |    |    |    | 1480 |   |    |    |    | 1485 |   |    |    |    |    |      |
| ggc | acc | act | tct | act | gtc | gaa | tca | gat | ata | ttg | acc | caa | aca | gat | 5108 |
| Gly | Thr | Thr | Ser | Thr | Val | Glu | Ser | Asp | Ile | Leu | Thr | Gln | Thr | Asp |      |
| 1490 |    |    |    | 1495 |   |    |    |    | 1500 |   |    |    |    |    |      |
| aga | gag | gtg | gct | ctg | cac | gaa | agg | agt | agc | tct | gtt | tcc | act | att | 5153 |
| Arg | Glu | Val | Ala | Leu | His | Glu | Arg | Ser | Ser | Ser | Val | Ser | Thr | Ile |      |
| 1505 |    |    |    | 1510 |   |    |    |    | 1515 |   |    |    |    |    |      |
| gac | act | gcc | cgg | ctg | att | caa | gct | ttt | ggc | cat | gaa | aga | gta | tgc | 5198 |
| Asp | Thr | Ala | Arg | Leu | Ile | Gln | Ala | Phe | Gly | His | Glu | Arg | Val | Cys |      |
| 1520 |    |    |    | 1525 |   |    |    |    | 1530 |   |    |    |    |    |      |
| ttg | tca | ccc | aga | cga | att | aaa | tta | tat | agc | agc | atc | acc | aac | caa | 5243 |
| Leu | Ser | Pro | Arg | Arg | Ile | Lys | Leu | Tyr | Ser | Ser | Ile | Thr | Asn | Gln |      |
| 1535 |    |    |    | 1540 |   |    |    |    | 1545 |   |    |    |    |    |      |
| cag | agg | aga | tac | ctt | gag | aag | cgg | agc | aaa | cac | agc | aag | aaa | gtg | 5288 |
| Gln | Arg | Arg | Tyr | Leu | Glu | Lys | Arg | Ser | Lys | His | Ser | Lys | Lys | Val |      |
| 1550 |    |    |    | 1555 |   |    |    |    | 1560 |   |    |    |    |    |      |
| ctg | aat | aca | ggt | cat | ccc | cta | gtg | act | tct | gag | cac | acc | aga | agg | 5333 |
| Leu | Asn | Thr | Gly | His | Pro | Leu | Val | Thr | Ser | Glu | His | Thr | Arg | Arg |      |
| 1565 |    |    |    | 1570 |   |    |    |    | 1575 |   |    |    |    |    |      |
| aga | cac | atc | cag | gta | gca | aac | cat | gtg | att | tct | tct | gac | tct | att | 5378 |
| Arg | His | Ile | Gln | Val | Ala | Asn | His | Val | Ile | Ser | Ser | Asp | Ser | Ile |      |
| 1580 |    |    |    | 1585 |   |    |    |    | 1590 |   |    |    |    |    |      |
| tcc | tct | tct | gcc | agt | agt | ttc | ctg | agc | tca | aac | tct | act | ttt | tgc | 5423 |
| Ser | Ser | Ser | Ala | Ser | Ser | Phe | Leu | Ser | Ser | Asn | Ser | Thr | Phe | Cys |      |
| 1595 |    |    |    | 1600 |   |    |    |    | 1605 |   |    |    |    |    |      |
| aac | aag | cag | aat | gta | cac | atg | tta | aac | aag | ggc | ata | caa | gca | ggt | 5468 |
| Asn | Lys | Gln | Asn | Val | His | Met | Leu | Asn | Lys | Gly | Ile | Gln | Ala | Gly |      |
| 1610 |    |    |    | 1615 |   |    |    |    | 1620 |   |    |    |    |    |      |
| aac | ttg | gag | att | gtg | aac | ggt | gcc | aaa | aaa | cac | act | cga | gat | gtt | 5513 |
| Asn | Leu | Glu | Ile | Val | Asn | Gly | Ala | Lys | Lys | His | Thr | Arg | Asp | Val |      |
| 1625 |    |    |    | 1630 |   |    |    |    | 1635 |   |    |    |    |    |      |

```
ggg  ata  act  ttc  cca  act  cca  agt  tcc  agc  gag  gct  aaa  ttg  gaa    5558
Gly  Ile  Thr  Phe  Pro  Thr  Pro  Ser  Ser  Ser  Glu  Ala  Lys  Leu  Glu
1640                1645                         1650 gag  aac  agt  gat  gtg  act  tct  tgg  tca  gaa  gaa  aaa  cgt  gaa  gag    5603
Glu  Asn  Ser  Asp  Val  Thr  Ser  Trp  Ser  Glu  Glu  Lys  Arg  Glu  Glu
1655                1660                         1665 aaa  atg  ctc  ttt  acc  ggt  tat  cct  gag  gac  aga  aag  tta  aaa  aag    5648
Lys  Met  Leu  Phe  Thr  Gly  Tyr  Pro  Glu  Asp  Arg  Lys  Leu  Lys  Lys
1670                1675                         1680 aac  aag  aag  aat  tcc  cat  gaa  gga  gtt  tcc  tgg  ttt  gtt  cct  gtg    5693
Asn  Lys  Lys  Asn  Ser  His  Glu  Gly  Val  Ser  Trp  Phe  Val  Pro  Val
1685                1690                         1695 gaa  aat  gtg  gag  tct  aga  tca  aag  aag  gaa  aac  gtg  cct  aac  act    5738
Glu  Asn  Val  Glu  Ser  Arg  Ser  Lys  Lys  Glu  Asn  Val  Pro  Asn  Thr
1700                1705                         1710 tgt  ggc  cct  ggc  atc  tcc  tgg  ttt  gaa  cca  ata  acc  aag  acc  aga    5783
Cys  Gly  Pro  Gly  Ile  Ser  Trp  Phe  Glu  Pro  Ile  Thr  Lys  Thr  Arg
1715                1720                         1725 ccc  tgg  agg  gag  cca  ctg  cgg  gag  cag  aac  tgt  cag  ggg  cag  cac    5828
Pro  Trp  Arg  Glu  Pro  Leu  Arg  Glu  Gln  Asn  Cys  Gln  Gly  Gln  His
1730                1735                         1740 ctg  gac  ggt  cgg  ggc  tac  ctg  gca  ggc  cca  ggc  aga  gag  gct  ggc    5873
Leu  Asp  Gly  Arg  Gly  Tyr  Leu  Ala  Gly  Pro  Gly  Arg  Glu  Ala  Gly
1745                1750                         1755 aga  gac  cta  ctg  aag  cca  ttt  gtg  aga  gca  acc  ctt  cag  gaa  tcg    5918
Arg  Asp  Leu  Leu  Lys  Pro  Phe  Val  Arg  Ala  Thr  Leu  Gln  Glu  Ser
1760                1765                         1770 ctt  cag  ttt  cac  aga  cct  gac  ttc  atc  tcc  cgc  tct  ggg  gag  cgg    5963
Leu  Gln  Phe  His  Arg  Pro  Asp  Phe  Ile  Ser  Arg  Ser  Gly  Glu  Arg
1775                1780                         1785 ata  aag  cgc  ctg  aag  tta  ata  gtc  cag  gag  agg  aag  ctg  cag  agc    6008
Ile  Lys  Arg  Leu  Lys  Leu  Ile  Val  Gln  Glu  Arg  Lys  Leu  Gln  Ser
1790                1795                         1800 atg  tta  cag  acc  gag  cgg  gat  gca  cta  ttc  aac  att  gac  agg  gaa    6053
Met  Leu  Gln  Thr  Glu  Arg  Asp  Ala  Leu  Phe  Asn  Ile  Asp  Arg  Glu
1805                1810                         1815 cgg  cag  ggc  cac  cag  aat  cgc  atg  tgc  ccg  ctg  ccc  aag  aga  gtc    6098
Arg  Gln  Gly  His  Gln  Asn  Arg  Met  Cys  Pro  Leu  Pro  Lys  Arg  Val
1820                1825                         1830 ttc  ctg  gct  atc  cag  aag  aac  aag  cct  atc  agc  aag  aag  gaa  atg    6143
Phe  Leu  Ala  Ile  Gln  Lys  Asn  Lys  Pro  Ile  Ser  Lys  Lys  Glu  Met
1835                1840                         1845 att  cag  agg  tcc  aaa  cgg  att  tat  gag  cag  ctt  cca  gaa  gta  cag    6188
Ile  Gln  Arg  Ser  Lys  Arg  Ile  Tyr  Glu  Gln  Leu  Pro  Glu  Val  Gln
1850                1855                         1860 aaa  aag  aga  gaa  gaa  gag  aag  aga  aaa  tca  gaa  tat  aag  tca  tac    6233
Lys  Lys  Arg  Glu  Glu  Glu  Lys  Arg  Lys  Ser  Glu  Tyr  Lys  Ser  Tyr
1865                1870                         1875 cgg  ctg  cga  gcc  cag  cta  tat  aaa  aag  aga  gtg  acc  aat  caa  ctt    6278
Arg  Leu  Arg  Ala  Gln  Leu  Tyr  Lys  Lys  Arg  Val  Thr  Asn  Gln  Leu
1880                1885                         1890 ctg  ggg  aga  aaa  gtt  ccc  tgg  gac  tgacacaagt  ttattttcct                 6322
Leu  Gly  Arg  Lys  Val  Pro  Trp  Asp
1895                1900 cagagccttg gaattctatt ttatgaacct agagaagcag aatccttact tttgtgagtc             6382
tggttgaata aagcttattc tttgtccatg tgtattttag aaatagtaac ttctaaagag             6442
tctggaacaa agtggtgatt aaaattccta atggtttggg agcaatactt tctgcatagt             6502
```

-continued

```
ggccttgtcc aatggcctgt gtgttacaat gatatgatca tttctcaaga ataagtccct    6562
ttttgtatgt gttttatac ttttagaaaa taaaaacttt agattaactc                6612
```

<210> SEQ ID NO 2
<211> LENGTH: 1902
<212> TYPE: PRT
<213> ORGANISM: Homo sapiens

<400> SEQUENCE: 2

```
Met Glu Ala Glu Asn Met Ala Leu Lys Arg Cys Asn Phe Pro Ala Pro
1               5                   10                  15

Leu Ala Arg Phe Arg Asp Ile Ser Asp Ile Ser Phe Ile Gln Ser Lys
            20                  25                  30

Lys Val Val Cys Phe Lys Glu Pro Ser Ser Thr Gly Val Ser Asn Gly
        35                  40                  45

Asp Leu Leu His Arg Gln Pro Phe Thr Glu Glu Ser Pro Ser Ser Arg
    50                  55                  60

Cys Ile Gln Lys Asp Ile Gly Thr Gln Thr Asn Leu Lys Cys Arg Arg
65                  70                  75                  80

Gly Ile Glu Asn Trp Glu Phe Ile Ser Ser Thr Thr Val Arg Ser Pro
                85                  90                  95

Leu Gln Glu Ala Glu Ser Lys Val Ser Met Ala Leu Glu Glu Thr Leu
            100                 105                 110

Arg Gln Tyr Gln Ala Ala Lys Ser Val Met Arg Ser Glu Pro Glu Gly
        115                 120                 125

Cys Ser Gly Thr Ile Gly Asn Lys Ile Ile Ile Pro Met Met Thr Val
    130                 135                 140

Ile Lys Ser Asp Ser Ser Ser Asp Ala Ser Asp Gly Asn Gly Ser Cys
145                 150                 155                 160

Ser Trp Asp Ser Asn Leu Pro Glu Ser Leu Glu Ser Val Ser Asp Val
                165                 170                 175

Leu Leu Asn Phe Phe Pro Tyr Val Ser Pro Lys Thr Ser Ile Thr Asp
            180                 185                 190

Ser Arg Glu Glu Glu Gly Val Ser Glu Ser Asp Gly Gly Ser
        195                 200                 205

Ser Val Asp Ser Leu Ala Ala His Val Lys Asn Leu Leu Gln Cys Glu
    210                 215                 220

Ser Ser Leu Asn His Ala Lys Glu Ile Leu Arg Asn Ala Glu Glu Glu
225                 230                 235                 240

Glu Ser Arg Val Arg Ala His Ala Trp Asn Met Lys Phe Asn Leu Ala
                245                 250                 255

His Asp Cys Gly Tyr Ser Ile Ser Glu Leu Asn Glu Asp Asp Arg Arg
            260                 265                 270

Lys Val Glu Glu Ile Lys Ala Glu Leu Phe Gly His Gly Arg Thr Thr
        275                 280                 285

Asp Leu Ser Lys Gly Leu Gln Ser Pro Arg Gly Met Gly Cys Lys Pro
    290                 295                 300

Glu Ala Val Cys Ser His Ile Ile Ile Glu Ser Glu Lys Gly Cys
305                 310                 315                 320

Phe Arg Thr Leu Thr Ser Glu His Pro Gln Leu Asp Arg His Pro Cys
                325                 330                 335

Ala Phe Arg Ser Ala Gly Pro Ser Glu Met Thr Arg Gly Arg Gln Asn
            340                 345                 350

Pro Ser Ser Cys Arg Ala Lys His Val Asn Leu Ser Ala Ser Leu Asp
```

-continued

```
                355                 360                 365
Gln Asn Asn Ser His Phe Lys Val Trp Asn Ser Leu Gln Leu Lys Ser
            370                 375                 380

His Ser Pro Phe Gln Asn Phe Ile Pro Asp Glu Phe Lys Ile Ser Lys
385                 390                 395                 400

Gly Leu Arg Met Pro Phe Asp Glu Lys Met Asp Pro Trp Leu Ser Glu
                405                 410                 415

Leu Val Glu Pro Ala Phe Val Pro Pro Lys Glu Val Asp Phe His Ser
            420                 425                 430

Ser Ser Gln Met Pro Ser Pro Glu Pro Met Lys Lys Phe Thr Thr Ser
        435                 440                 445

Ile Thr Phe Ser Ser His Arg His Ser Lys Cys Ile Ser Asn Ser Ser
    450                 455                 460

Val Val Lys Val Gly Val Thr Glu Gly Ser Gln Cys Thr Gly Ala Ser
465                 470                 475                 480

Val Gly Val Phe Asn Ser His Phe Thr Glu Glu Gln Asn Pro Pro Arg
                485                 490                 495

Asp Leu Lys Gln Lys Thr Ser Ser Pro Ser Ser Phe Lys Met His Ser
            500                 505                 510

Asn Ser Gln Asp Lys Glu Val Thr Ile Leu Ala Glu Gly Arg Arg Gln
        515                 520                 525

Ser Gln Lys Leu Pro Val Asp Phe Glu Arg Ser Phe Gln Glu Glu Lys
    530                 535                 540

Pro Leu Glu Arg Ser Asp Phe Thr Gly Ser His Ser Glu Pro Ser Thr
545                 550                 555                 560

Arg Ala Asn Cys Ser Asn Phe Lys Glu Ile Gln Ile Ser Asp Asn His
                565                 570                 575

Thr Leu Ile Ser Met Gly Arg Pro Ser Ser Thr Leu Gly Val Asn Arg
            580                 585                 590

Ser Ser Ser Arg Leu Gly Val Lys Glu Lys Asn Val Thr Ile Thr Pro
        595                 600                 605

Asp Leu Pro Ser Cys Ile Phe Leu Glu Gln Arg Glu Leu Phe Glu Gln
    610                 615                 620

Ser Lys Ala Pro Arg Ala Asp Asp His Val Arg Lys His His Ser Pro
625                 630                 635                 640

Ser Pro Gln His Gln Asp Tyr Val Ala Pro Asp Leu Pro Ser Cys Ile
                645                 650                 655

Phe Leu Glu Gln Arg Glu Leu Phe Glu Gln Cys Lys Ala Pro Tyr Val
            660                 665                 670

Asp His Gln Met Arg Glu Asn His Ser Pro Leu Pro Gln Gly Gln Asp
        675                 680                 685

Ser Ile Ala Ser Asp Leu Pro Ser Pro Ile Ser Leu Glu Gln Cys Gln
    690                 695                 700

Ser Lys Ala Pro Gly Val Asp Asp Gln Met Asn Lys His His Phe Pro
705                 710                 715                 720

Leu Pro Gln Gly Gln Asp Cys Val Val Glu Lys Asn Asn Gln His Lys
                725                 730                 735

Pro Lys Ser His Ile Ser Asn Ile Asn Val Glu Ala Lys Phe Asn Thr
            740                 745                 750

Val Val Ser Gln Ser Ala Pro Asn His Cys Thr Leu Ala Ala Ser Ala
        755                 760                 765

Ser Thr Pro Pro Ser Asn Arg Lys Ala Leu Ser Cys Val His Ile Thr
    770                 775                 780
```

-continued

```
Leu Cys Pro Lys Thr Ser Ser Lys Leu Asp Ser Gly Thr Leu Asp Glu
785                 790                 795                 800

Arg Phe His Ser Leu Asp Ala Ala Ser Lys Ala Arg Met Asn Ser Glu
            805                 810                 815

Phe Asn Phe Asp Leu His Thr Val Ser Ser Arg Ser Leu Glu Pro Thr
            820                 825                 830

Ser Lys Leu Leu Thr Ser Lys Pro Val Ala Gln Asp Gln Glu Ser Leu
            835                 840                 845

Gly Phe Leu Gly Pro Lys Ser Ser Leu Asp Phe Gln Val Val Gln Pro
850                 855                 860

Ser Leu Pro Asp Ser Asn Thr Ile Thr Gln Asp Leu Lys Thr Ile Pro
865                 870                 875                 880

Ser Gln Asn Ser Gln Ile Val Thr Ser Arg Gln Ile Gln Val Asn Ile
            885                 890                 895

Ser Asp Phe Glu Gly His Ser Asn Pro Glu Gly Thr Pro Val Phe Ala
            900                 905                 910

Asp Arg Leu Pro Glu Lys Met Lys Thr Pro Leu Ser Ala Phe Ser Glu
            915                 920                 925

Lys Leu Ser Ser Asp Ala Val Thr Gln Ile Thr Thr Glu Ser Pro Glu
930                 935                 940

Lys Thr Leu Phe Ser Ser Glu Ile Phe Ile Asn Ala Glu Asp Arg Gly
945                 950                 955                 960

His Glu Ile Ile Glu Pro Gly Asn Gln Lys Leu Arg Lys Ala Pro Val
            965                 970                 975

Lys Phe Ala Ser Ser Ser Ser Val Gln Gln Val Thr Phe Ser Arg Gly
            980                 985                 990

Thr Asp Gly Gln Pro Leu Leu Leu Pro Tyr Lys Pro Ser Gly Ser Thr
            995                1000                1005

Lys Met Tyr Tyr Val Pro Gln Leu Arg Gln Ile Pro Pro Ser Pro
    1010                1015                1020

Asp Ser Lys Ser Asp Thr Thr Val Glu Ser Ser His Ser Gly Ser
    1025                1030                1035

Asn Asp Ala Ile Ala Pro Asp Phe Pro Ala Gln Val Leu Gly Thr
    1040                1045                1050

Arg Asp Asp Asp Leu Ser Ala Thr Val Asn Ile Lys His Lys Glu
    1055                1060                1065

Gly Ile Tyr Ser Lys Arg Val Val Thr Lys Ala Ser Leu Pro Val
    1070                1075                1080

Gly Glu Lys Pro Leu Gln Asn Glu Asn Ala Asp Ala Ser Val Gln
    1085                1090                1095

Val Leu Ile Thr Gly Asp Glu Asn Leu Ser Asp Lys Lys Gln Gln
    1100                1105                1110

Glu Ile His Ser Thr Arg Ala Val Thr Glu Ala Ala Gln Ala Lys
    1115                1120                1125

Glu Lys Glu Ser Leu Gln Lys Asp Thr Ala Asp Ser Ser Ala Ala
    1130                1135                1140

Ala Ala Ala Glu His Ser Ala Gln Val Gly Asp Pro Glu Met Lys
    1145                1150                1155

Asn Leu Pro Asp Thr Lys Ala Ile Thr Gln Lys Glu Glu Ile His
    1160                1165                1170

Arg Lys Lys Thr Val Pro Glu Glu Ala Trp Pro Asn Asn Lys Glu
    1175                1180                1185
```

-continued

```
Ser Leu Gln Ile Asn Ile Glu Glu Ser Glu Cys His Ser Glu Phe
    1190                1195                1200

Glu Asn Thr Thr Arg Ser Val Phe Arg Ser Ala Lys Phe Tyr Ile
    1205                1210                1215

His His Pro Val His Leu Pro Ser Asp Gln Asp Ile Cys His Glu
    1220                1225                1230

Ser Leu Gly Lys Ser Val Phe Met Arg His Ser Trp Lys Asp Phe
    1235                1240                1245

Phe Gln His His Pro Asp Lys His Arg Glu His Met Cys Leu Pro
    1250                1255                1260

Leu Pro Tyr Gln Asn Met Asp Lys Thr Lys Thr Asp Tyr Thr Arg
    1265                1270                1275

Ile Lys Ser Leu Ser Ile Asn Val Asn Leu Gly Asn Lys Glu Val
    1280                1285                1290

Met Asp Thr Thr Lys Ser Gln Val Arg Asp Tyr Pro Lys His Asn
    1295                1300                1305

Gly Gln Ile Ser Asp Pro Gln Arg Asp Gln Lys Val Thr Pro Glu
    1310                1315                1320

Gln Thr Thr Gln His Thr Val Ser Leu Asn Glu Leu Trp Asn Lys
    1325                1330                1335

Tyr Arg Glu Arg Gln Arg Gln Arg Gln Pro Glu Leu Gly Asp
    1340                1345                1350

Arg Lys Glu Leu Ser Leu Val Asp Arg Leu Asp Arg Leu Ala Lys
    1355                1360                1365

Ile Leu Gln Asn Pro Ile Thr His Ser Leu Gln Val Ser Glu Ser
    1370                1375                1380

Thr His Asp Asp Ser Arg Gly Glu Arg Ser Val Lys Glu Trp Ser
    1385                1390                1395

Gly Arg Gln Gln Gln Arg Asn Lys Leu Gln Lys Lys Arg Phe
    1400                1405                1410

Lys Ser Leu Glu Lys Ser His Lys Asn Thr Gly Glu Leu Lys Lys
    1415                1420                1425

Ser Lys Val Leu Ser His His Arg Ala Gly Arg Ser Asn Gln Ile
    1430                1435                1440

Lys Ile Glu Gln Ile Lys Phe Asp Lys Tyr Ile Leu Ser Lys Gln
    1445                1450                1455

Pro Gly Phe Asn Tyr Ile Ser Asn Thr Ser Ser Asp Cys Arg Pro
    1460                1465                1470

Ser Glu Glu Ser Glu Leu Leu Thr Asp Thr Thr Asn Ile Leu
    1475                1480                1485

Ser Gly Thr Thr Ser Thr Val Glu Ser Asp Ile Leu Thr Gln Thr
    1490                1495                1500

Asp Arg Glu Val Ala Leu His Glu Arg Ser Ser Val Ser Thr
    1505                1510                1515

Ile Asp Thr Ala Arg Leu Ile Gln Ala Phe Gly His Glu Arg Val
    1520                1525                1530

Cys Leu Ser Pro Arg Arg Ile Lys Leu Tyr Ser Ser Ile Thr Asn
    1535                1540                1545

Gln Gln Arg Arg Tyr Leu Glu Lys Arg Ser Lys His Ser Lys Lys
    1550                1555                1560

Val Leu Asn Thr Gly His Pro Leu Val Thr Ser Glu His Thr Arg
    1565                1570                1575

Arg Arg His Ile Gln Val Ala Asn His Val Ile Ser Ser Asp Ser
```

```
            1580                1585                1590

Ile Ser Ser Ser Ala Ser Ser Phe Leu Ser Ser Asn Ser Thr Phe
    1595                1600                1605

Cys Asn Lys Gln Asn Val His Met Leu Asn Lys Gly Ile Gln Ala
    1610                1615                1620

Gly Asn Leu Glu Ile Val Asn Gly Ala Lys Lys His Thr Arg Asp
    1625                1630                1635

Val Gly Ile Thr Phe Pro Thr Pro Ser Ser Ser Glu Ala Lys Leu
    1640                1645                1650

Glu Glu Asn Ser Asp Val Thr Ser Trp Ser Glu Lys Arg Glu
    1655                1660                1665

Glu Lys Met Leu Phe Thr Gly Tyr Pro Glu Asp Arg Lys Leu Lys
    1670                1675                1680

Lys Asn Lys Lys Asn Ser His Glu Gly Val Ser Trp Phe Val Pro
    1685                1690                1695

Val Glu Asn Val Glu Ser Arg Ser Lys Lys Glu Asn Val Pro Asn
    1700                1705                1710

Thr Cys Gly Pro Gly Ile Ser Trp Phe Glu Pro Ile Thr Lys Thr
    1715                1720                1725

Arg Pro Trp Arg Glu Pro Leu Arg Glu Gln Asn Cys Gln Gly Gln
    1730                1735                1740

His Leu Asp Gly Arg Gly Tyr Leu Ala Gly Pro Gly Arg Glu Ala
    1745                1750                1755

Gly Arg Asp Leu Leu Lys Pro Phe Val Arg Ala Thr Leu Gln Glu
    1760                1765                1770

Ser Leu Gln Phe His Arg Pro Asp Phe Ile Ser Arg Ser Gly Glu
    1775                1780                1785

Arg Ile Lys Arg Leu Lys Leu Ile Val Gln Glu Arg Lys Leu Gln
    1790                1795                1800

Ser Met Leu Gln Thr Glu Arg Asp Ala Leu Phe Asn Ile Asp Arg
    1805                1810                1815

Glu Arg Gln Gly His Gln Asn Arg Met Cys Pro Leu Pro Lys Arg
    1820                1825                1830

Val Phe Leu Ala Ile Gln Lys Asn Lys Pro Ile Ser Lys Lys Glu
    1835                1840                1845

Met Ile Gln Arg Ser Lys Arg Ile Tyr Glu Gln Leu Pro Glu Val
    1850                1855                1860

Gln Lys Lys Arg Glu Glu Lys Lys Arg Lys Ser Glu Tyr Lys Ser
    1865                1870                1875

Tyr Arg Leu Arg Ala Gln Leu Tyr Lys Lys Arg Val Thr Asn Gln
    1880                1885                1890

Leu Leu Gly Arg Lys Val Pro Trp Asp
    1895                1900

<210> SEQ ID NO 3
<211> LENGTH: 21
<212> TYPE: DNA
<213> ORGANISM: Artificial Sequence
<220> FEATURE:
<223> OTHER INFORMATION: One-half of primer pair for exon 1 of ALMS1
      for mutation analysis

<400> SEQUENCE: 3
tgcaggtttt agagatgttg g                                            21
```

```
<210> SEQ ID NO 4
<211> LENGTH: 21
<212> TYPE: DNA
<213> ORGANISM: Artificial Sequence
<220> FEATURE:
<223> OTHER INFORMATION: One-half of primer pair for exon 1 of ALMS1
      for mutation analysis

<400> SEQUENCE: 4
tgcttgtatt tttcattggc t                                          21

<210> SEQ ID NO 5
<211> LENGTH: 21
<212> TYPE: DNA
<213> ORGANISM: Artificial Sequence
<220> FEATURE:
<223> OTHER INFORMATION: One-half of primer pair for exon 2 of ALMS1
      for mutation analysis

<400> SEQUENCE: 5
catactaagc attgcagtgg g                                          21

<210> SEQ ID NO 6
<211> LENGTH: 21
<212> TYPE: DNA
<213> ORGANISM: Artificial Sequence
<220> FEATURE:
<223> OTHER INFORMATION: One-half of primer pair for exon 2 of ALMS1
      for mutation analysis

<400> SEQUENCE: 6
gaatgggtga tggaattagg a                                          21

<210> SEQ ID NO 7
<211> LENGTH: 21
<212> TYPE: DNA
<213> ORGANISM: Artificial Sequence
<220> FEATURE:
<223> OTHER INFORMATION: One-half of primer pair for exon 3 of ALMS1
      for mutation analysis

<400> SEQUENCE: 7
tggtctaatc ttagcgtggg t                                          21

<210> SEQ ID NO 8
<211> LENGTH: 21
<212> TYPE: DNA
<213> ORGANISM: Artificial Sequence
<220> FEATURE:
<223> OTHER INFORMATION: One-half of primer pair for exon 3 of ALMS1
      for mutation analysis

<400> SEQUENCE: 8
ccgtgtgatt tctctgagtg g                                          21

<210> SEQ ID NO 9
<211> LENGTH: 22
<212> TYPE: DNA
<213> ORGANISM: Artificial Sequence
<220> FEATURE:
<223> OTHER INFORMATION: One-half of primer pair for exon 4 of ALMS1
      for mutation analysis

<400> SEQUENCE: 9
ttgacattga tgtgtccaca at                                         22

<210> SEQ ID NO 10
```

```
<211> LENGTH: 22
<212> TYPE: DNA
<213> ORGANISM: Artificial Sequence
<220> FEATURE:
<223> OTHER INFORMATION: One-half of primer pair for exon 4 of ALMS1
      for mutation analysis

<400> SEQUENCE: 10
atttgcatag ctgtcaacag aa                                              22

<210> SEQ ID NO 11
<211> LENGTH: 21
<212> TYPE: DNA
<213> ORGANISM: Artificial Sequence
<220> FEATURE:
<223> OTHER INFORMATION: One-half of primer pair for exon 5 of ALMS1
      for mutation analysis

<400> SEQUENCE: 11
gcctgaaaca tagaaggcat t                                               21

<210> SEQ ID NO 12
<211> LENGTH: 21
<212> TYPE: DNA
<213> ORGANISM: Artificial Sequence
<220> FEATURE:
<223> OTHER INFORMATION: One-half of primer pair for exon 5 of ALMS1
      for mutation analysis

<400> SEQUENCE: 12
ggagtgacaa aagtccagtg c                                               21

<210> SEQ ID NO 13
<211> LENGTH: 22
<212> TYPE: DNA
<213> ORGANISM: Artificial Sequence
<220> FEATURE:
<223> OTHER INFORMATION: One-half of primer pair for exon 6 of ALMS1
      for mutation analysis

<400> SEQUENCE: 13
ctcaatctca tgtcgctatt tg                                              22

<210> SEQ ID NO 14
<211> LENGTH: 22
<212> TYPE: DNA
<213> ORGANISM: Artificial Sequence
<220> FEATURE:
<223> OTHER INFORMATION: One-half of primer pair for exon 6 of ALMS1
      for mutation analysis

<400> SEQUENCE: 14
tgctcaatat aacagcaagg ag                                              22

<210> SEQ ID NO 15
<211> LENGTH: 21
<212> TYPE: DNA
<213> ORGANISM: Artificial Sequence
<220> FEATURE:
<223> OTHER INFORMATION: One-half of primer pair for exon 7 of ALMS1
      for mutation analysis

<400> SEQUENCE: 15
gggttttgtt tgtaattgtg g                                               21

<210> SEQ ID NO 16
<211> LENGTH: 22
```

-continued

```
<212> TYPE: DNA
<213> ORGANISM: Artificial Sequence
<220> FEATURE:
<223> OTHER INFORMATION: One-half of primer pair for exon 7 of ALMS1
      for mutation analysis

<400> SEQUENCE: 16
gagagctgaa gacagcaaga ag                                              22

<210> SEQ ID NO 17
<211> LENGTH: 21
<212> TYPE: DNA
<213> ORGANISM: Artificial Sequence
<220> FEATURE:
<223> OTHER INFORMATION: One-half of primer pair for exon 8 of ALMS1
      for mutation analysis

<400> SEQUENCE: 17
cgctacctct ttttctgact g                                               21

<210> SEQ ID NO 18
<211> LENGTH: 22
<212> TYPE: DNA
<213> ORGANISM: Artificial Sequence
<220> FEATURE:
<223> OTHER INFORMATION: One-half of primer pair for exon 8 of ALMS1
      for mutation analysis

<400> SEQUENCE: 18
tggaaacact aacactgacc ct                                              22

<210> SEQ ID NO 19
<211> LENGTH: 21
<212> TYPE: DNA
<213> ORGANISM: Artificial Sequence
<220> FEATURE:
<223> OTHER INFORMATION: One-half of primer pair for exon 9 of ALMS1
      for mutation analysis

<400> SEQUENCE: 19
gaggctacta agcaacaagg c                                               21

<210> SEQ ID NO 20
<211> LENGTH: 19
<212> TYPE: DNA
<213> ORGANISM: Artificial Sequence
<220> FEATURE:
<223> OTHER INFORMATION: One-half of primer pair for exon 9 of ALMS1
      for mutation analysis

<400> SEQUENCE: 20
gcagtcacat tgccagatg                                                  19

<210> SEQ ID NO 21
<211> LENGTH: 19
<212> TYPE: DNA
<213> ORGANISM: Artificial Sequence
<220> FEATURE:
<223> OTHER INFORMATION: One-half of primer pair for exon 10 of ALMS1
      for mutation analysis

<400> SEQUENCE: 21
tggcttgctt atcctgtgg                                                  19

<210> SEQ ID NO 22
<211> LENGTH: 21
<212> TYPE: DNA
```

―continued

```
<213> ORGANISM: Artificial Sequence
<220> FEATURE:
<223> OTHER INFORMATION: One-half of primer pair for exon 10 of ALMS1
      for mutation analysis

<400> SEQUENCE: 22
tctgacaaga tgaaaattgg c                                              21

<210> SEQ ID NO 23
<211> LENGTH: 21
<212> TYPE: DNA
<213> ORGANISM: Artificial Sequence
<220> FEATURE:
<223> OTHER INFORMATION: One-half of primer pair for exon 11 of ALMS1
      for mutation analysis

<400> SEQUENCE: 23
tcccagagac acctatgatc c                                              21

<210> SEQ ID NO 24
<211> LENGTH: 21
<212> TYPE: DNA
<213> ORGANISM: Artificial Sequence
<220> FEATURE:
<223> OTHER INFORMATION: One-half of primer pair for exon 11 of ALMS1
      for mutation analysis

<400> SEQUENCE: 24
cttggagttg ggaaagttat c                                              21

<210> SEQ ID NO 25
<211> LENGTH: 25
<212> TYPE: DNA
<213> ORGANISM: Artificial Sequence
<220> FEATURE:
<223> OTHER INFORMATION: One-half of primer pair for exon 12 of ALMS1
      for mutation analysis

<400> SEQUENCE: 25
gccaaaaaac acactcgaga tgttg                                          25

<210> SEQ ID NO 26
<211> LENGTH: 20
<212> TYPE: DNA
<213> ORGANISM: Artificial Sequence
<220> FEATURE:
<223> OTHER INFORMATION: One-half of primer pair for exon 12 of ALMS1
      for mutation analysis

<400> SEQUENCE: 26
ccaagtcaca gagccagctt                                                20

<210> SEQ ID NO 27
<211> LENGTH: 21
<212> TYPE: DNA
<213> ORGANISM: Artificial Sequence
<220> FEATURE:
<223> OTHER INFORMATION: One-half of primer pair for exon 13 of ALMS1
      for mutation analysis

<400> SEQUENCE: 27
gcatatcctg gataagagct g                                              21

<210> SEQ ID NO 28
<211> LENGTH: 19
<212> TYPE: DNA
<213> ORGANISM: Artificial Sequence
```

-continued

<220> FEATURE:
<223> OTHER INFORMATION: One-half of primer pair for exon 13 of ALMS1
     for mutation analysis

<400> SEQUENCE: 28
gagaaaccca accctcgtg                                              19

<210> SEQ ID NO 29
<211> LENGTH: 20
<212> TYPE: DNA
<213> ORGANISM: Artificial Sequence
<220> FEATURE:
<223> OTHER INFORMATION: One-half of primer pair for exon 14 of ALMS1
     for mutation analysis

<400> SEQUENCE: 29
tcagacttcc ccaaacctct                                             20

<210> SEQ ID NO 30
<211> LENGTH: 22
<212> TYPE: DNA
<213> ORGANISM: Artificial Sequence
<220> FEATURE:
<223> OTHER INFORMATION: One-half of primer pair for exon 14 of ALMS1
     for mutation analysis

<400> SEQUENCE: 30
tcagtgccat aagtgagaaa tg                                          22

<210> SEQ ID NO 31
<211> LENGTH: 20
<212> TYPE: DNA
<213> ORGANISM: Artificial Sequence
<220> FEATURE:
<223> OTHER INFORMATION: One-half of primer pair for exon 15 of ALMS1
     for mutation analysis

<400> SEQUENCE: 31
gactctgcac cctggtaacc                                             20

<210> SEQ ID NO 32
<211> LENGTH: 20
<212> TYPE: DNA
<213> ORGANISM: Artificial Sequence
<220> FEATURE:
<223> OTHER INFORMATION: One-half of primer pair for exon 15 of ALMS1
     for mutation analysis

<400> SEQUENCE: 32
cgccaataaa cctgatccat                                             20

<210> SEQ ID NO 33
<211> LENGTH: 22
<212> TYPE: DNA
<213> ORGANISM: Artificial Sequence
<220> FEATURE:
<223> OTHER INFORMATION: One-half of primer pair for exon 16 of ALMS1
     for mutation analysis

<400> SEQUENCE: 33
gcctctgatg gcagtaatat ct                                          22

<210> SEQ ID NO 34
<211> LENGTH: 21
<212> TYPE: DNA
<213> ORGANISM: Artificial Sequence
<220> FEATURE:

-continued

```
<223> OTHER INFORMATION: One-half of primer pair for exon 16 of ALMS1
      for mutation analysis

<400> SEQUENCE: 34
tctccagatg ggaaagaatt g                                          21
```

ALSTRÖEM SYNDROME GENE, GENE VARIANTS, EXPRESSED PROTEIN AND METHODS OF DIAGNOSIS FOR ALSTRÖEM SYNDROME

PRIORITY TO RELATED APPLICATIONS

This application is a DIV of Ser. No. 10/292,576 filed Nov. 12, 2002 which is now ABN. This application claims the benefit of U.S. Provisional Application Ser. No. 60/345,883, filed Nov. 9, 2001.

FIELD OF THE INVENTION

The present invention relates to a nucleic acid sequence (SEQ ID NO:1) linked to Alström syndrome (ALMS1), variants of that nucleic acid sequence, the protein (SEQ ID NO:2) encoded by that nucleic acid sequence and screening methods for testing individuals to determine if they are carriers of Alström syndrome.

BACKGROUND OF THE INVENTION

Alström syndrome is a homogeneous autosomal recessive disorder that is characterized by childhood obesity associated with hyperinsulinemia, chronic hyperglycemia, and neurosensory deficits[3,4]. The Alström locus is likely to interact with genetic modifiers as subsets of patients present with additional features such as dilated cardiomyopathy[5], hepatic dysfunction[6], hypothyroidism[7], male hypogonadism, short stature and mild to moderate developmental delay and with secondary complications normally associated with type 2 diabetes, such as hyperlipidemia and atherosclerosis. The locus for Alström syndrome was initially mapped to chromosome 2p 13 in a large French Acadian kindred within a 14.9 cM region[8] and later to a refined interval of 6.1 cM[9,10].

SUMMARY OF THE INVENTION

Using a positional cloning strategy, we have identified previously uncharacterized transcript KIAA0328, in which mutation analysis revealed sequence variations including four frameshift mutations and two nonsense mutations in affected individuals from six unrelated families segregating for Alström Syndrome. ALMS1 is a novel gene that is ubiquitously expressed at low levels and does not share significant sequence homology with any other genes reported thus far. Identification of the ALMS1 gene provides us with an entry point into a novel pathway leading toward the understanding of both Alström Syndrome and the common diseases that characterize it phenotypically, such as obesity, hyperinsulinemia and hyperglycemia. The ALMS1 gene can be used to diagnose Alström Syndrome by genetic testing for mutations in the gene or testing for adequate production levels of the protein encoded by the gene in patient tissues. Identification of ALMS1 also enables screening of individuals to determine if they are carriers of Alström Syndrome by genetic testing.

BRIEF DESCRIPTION OF THE FIGURES

FIG. 5 Amino acid similarity between human (Residues 1770–1899 of SEQ ID NO: 2) and mouse ALMS1 (SEQ ID NO: 35) with mouse (AK016590) (SEQ ID NO: 37) and macaque (AB055273) (SEQ ID NO: 36) domains.

FIG. 6 ALMS1 β form cDNA sequence (SEQ ID NO:1) with the predicted 1902 amino acid encoded protein (SEQ ID NO: 2). The putative serine rich region (aa1590–1605), nuclear localization signals (aa1538–1563 and aa1670–1687) and the leucine zipper motif (aa213–234) is underlined. Polyadenylation signal sites are shown in bold.

FIG. 7 ALMS1 splice junctions. Figure discloses SEQ ID NOS: 38–68, respectively, in order of appearance.

FIG. 8 Primer pairs for ALMS1 mutation analysis. Figure discloses SEQ ID NOS: 3–34. respectively, in order of appearance.

DETAILED DESCRIPTION OF THE INVENTION

Figure 1:
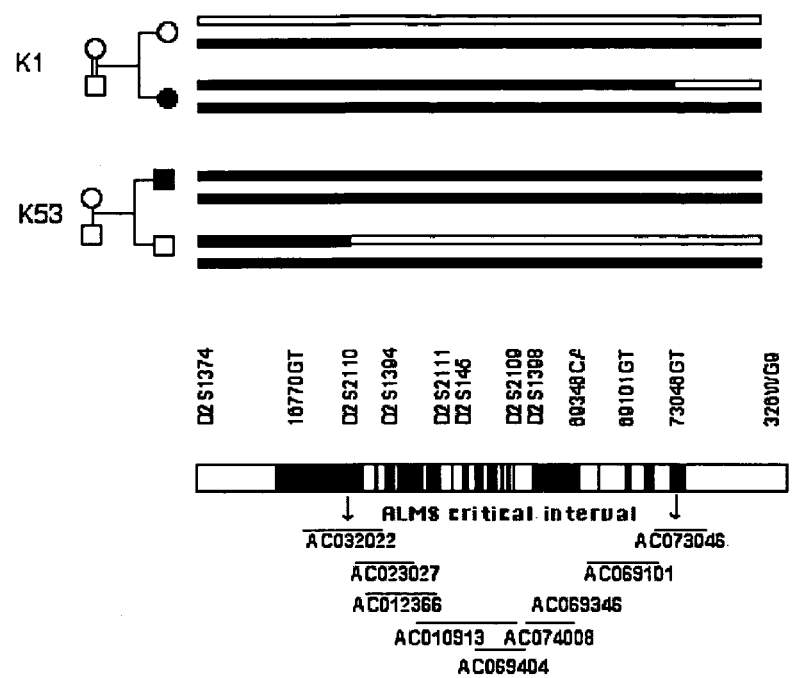
FIG. 1 Fine resolution and physical maps of the ALMS1 region. Recombinations in an affected child from the French Acadian kindred (I) and a child from a small nuclear family (II) place the ALMS1 critical interval in <2cM region. Eight overlapping BACs complete a 1.2 Mb contig. Locations of sixteen known and predicted genes derived from EST clusters are shown as darkened bars. Genes tested for mutation analysis are depicted with an asterisk. 1–16: SEC15 (AB023136), SPR (sepiapterin reductase), EMX1 (empty spiracle, drosophila homolog 1), THC529835 (c.elegans sre2 homolog), PP75 (KIAA0857), EST (THC551446), a novel gene related to EMX homeobox protein, NN8-4AG (retinoic acid responsive), CCT7 (chaperonin containing TCP1, subunit 7), EST (THC530316), EST (AI014261), EGR4 (early growth response 4), EST (KIAA0328), DUSP11 (dual-specificity phosphatase 11), AMSH (STAM-associated molecule), and ACTG2 (actin, gamma-2, smooth muscle, enteric).

Building on the prior art mapping of the Alström Syndrome to a 6.1 cM region of chromosome 2p13, further recombinational and physical mapping resolved the critical interval to <2 cM, encompassing a 1.2 Mb region (FIG. 1). The physical contig was assembled from publicly available sequence data (GenBank) by aligning overlapping BAC clones and adjoining fragments by transcription unit content. Candidate genes for mutation analysis were identified by comparing the contig sequence with sequences of identified genes and expressed sequence tag (EST) clusters using the NIX annotation pipeline[11] and individual database searches (Incyte Genomics and GenBank). We identified sixteen genes and EST clusters within the minimal interval. Candidate genes were initially prioritized based on their expression pattern and function. Subsequently, a systematic screening of all genes in the region was conducted.

One EST cluster, containing the novel cDNA sequence KIAA0328 (AB002326), was composed of cDNA fragments expressed in many tissues affected in Alström patients and thus, was subjected to mutation analysis. To obtain the full length coding sequence of the corresponding cDNA, alignments were made between KIAA0328 and overlapping transcripts (Incyte Genomics, NCBI, and TIGR). A total human cDNA sequence of 6,612 bp was derived with an open reading frame spanning 1902 amino acids (see FIG. 6). A translation initiation site was identified at nucleotide 597 and two putative polyadenylation sites (AATAAA) (SEQ ID NO: 75) was observed at positions 6389 and 6591, respectively. Alignment of the cDNA sequence with the genomic sequence identified 16 exons of varying lengths (45 through 1865 bp).

Figure 2:
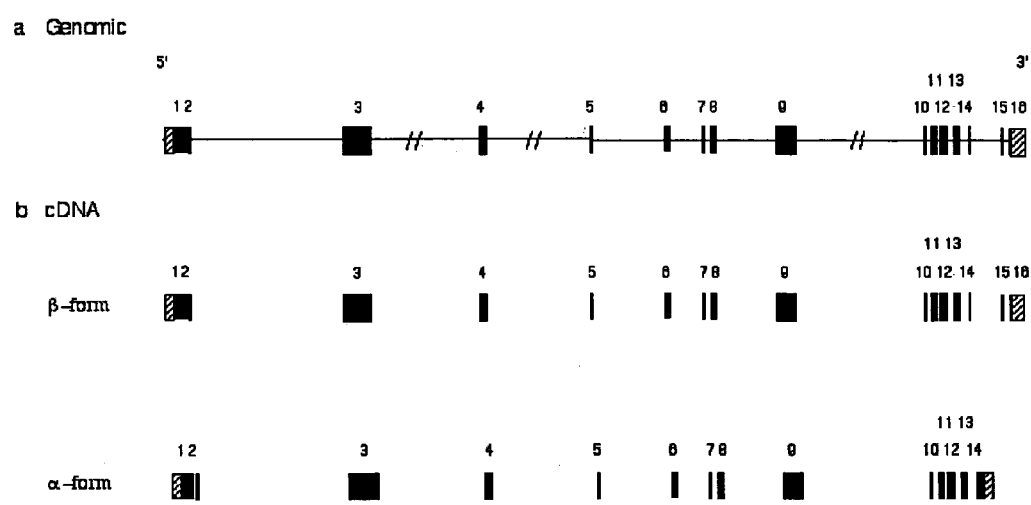
FIG. 2 Genomic structure and alternative splicing of the ALMS1 gene. a, Exon-intron structure of KIAA0328 (ALMS1) drawn to scale. The gene is comprised of 16 exons spanning >164 kb of genomic DNA. 5' and 3' UTR and exon regions are depicted by open and filled boxes, respectively. Introns for which there is incomplete sequence information are indicated by slash bars. b, Major alternative transcripts of human ALMS1.
Figure 3:
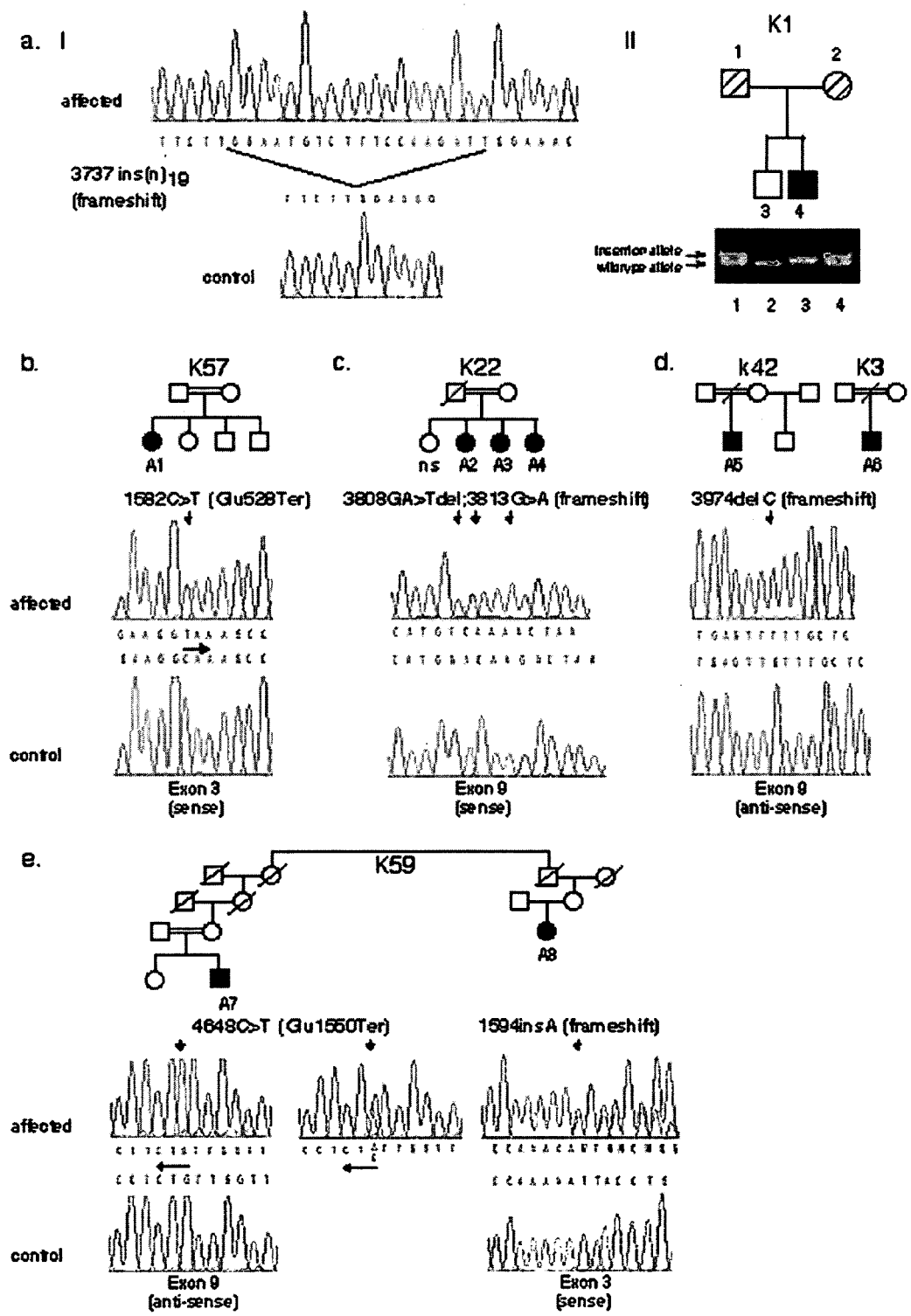
FIG. 3 Mutations in five unrelated families segregating for ALMS1. Mutations were observed in all affected subjects A1–A8. a–d, All mutations co-segregate with the disease in a homozygous state in affected individuals. a, Detection of a 19 bp insertion in exon 9 of KIAA0328 in a large consanguineous Acadian kindred (K1)[12]. Chromatogram displays the sequence variation between a normal control and an affected individual. PCR-amplification of the 19 bp insertion from a nuclear family within the Acadian kindred is shown on the right. The parents (1,2) are heterozygous for the mutation (carrier), the unaffected child (3) is homozygous for the normal allele (439 bp, non-carrier) and the affected child (4) is homozygous for the insertion (458 bp). The transmission of the insertion is in full agreement with previously reported haplotypes (not shown). b, A 1582C>T nonsense mutation in exon 3 of an affected individual of Italian descent. c, 3808GA>T;3813G>A mutations in exon 9 resulting in a frameshift in all 3 affected siblings of French descent. NS=no sample. d, A 3974de1C frameshift mutation in exon 9 in two kindreds. The genealogical relationship between these two has not been identified. A premature termination signal results at codon 1330. e, A 4648C>T nonsense mutation in second cousins A7 (homozygous) and A8 (heterozygous). A second mutation (1594insA) was identified in A8 which results in a frameshift.

The exon-intron structure of the KIAA0328 gene, now referred to as ALMS1, is shown in FIG. 2a. Two overlapping human BAC clones, ctd2005P16 and RPCI-582H21 (AC069346 and AC074008), encompass the entire genomic sequence of ~160 kb (coding exons). Several splice variants of ALMS1 have been identified from public and Incyte Genomics cDNA library databases (FIG. 2b). The relative abundance of the variants has been estimated from the number of GenBank clones representing the different sequences and the tissue distribution analysis reported in the Incyte Database. The most abundant variant is the β form (TIGR, THC530050) that consists of 16 exons. The carboxy terminal exons, 14 to 16, are not represented in the originally identified α transcript (GenBank, AB002326), which utilizes an alternate polyadenylation site in intron 14. The predicted open reading frame of the a form terminates immediately after exon 14. Sequence analysis predicts that the β protein product (1902 aa) only differs from the α protein product (1855 aa) by a 47 aa extension at the C-terminus. Database searches also identified other rare variant sequences including a δ form (GenBank, W11846; Incyte, 1453614.1), which has a shortened 3$^{rd}$ exon, presumably due to the use of an internal splice donor site in exon 3, an ε variant sequence (Incyte, 1453614.3) which has a 5' extended exon 13 and a 3' extended exon 14, and a φ variant (GenBank, AWO82244) which is the result of the processing of an intron in the 3' noncoding region and which utilizes a polyadenylation signal 867 bps downstream of that of the β variant (not shown). These variants are expressed in a variety of tissues including brain, adrenal glands, lung, and testes.

Intronic primers were designed to amplify and sequence the entire coding region in DNA from six unrelated individuals affected with Alström syndrome. In the large consanguineous Acadian kindred[12] (K1), a 19 bp insertion was identified in exon 9 (FIG. 3a) which causes a frameshift resulting in early termination at codon 1263. The insertion was present in a homozygous state in all five affected subjects in the kindred. Transmission of the insertion allele in unaffected carriers was consistent with previously reported haplotypes[8]. The insertion allele was not observed in 100 unrelated individuals from the general population. Five additional mutations were identified in five unrelated families of diverse ethnicity (FIG. 3b–e, Table 1). All mutations segregated with ALMS1. In a consanguineous Italian family (K57), a homozygous mutation was identified, 1582C>T, generating a TAA termination signal, while in a consanguineous French family (K22), a frameshift mutation, 3808GA>T;3813G>A, resulting in an early termination signal at codon 1279, was observed in three affected siblings. In a consanguineous Portugese family (K59), a TAA nonsense mutation, 4648C>T, was identified in two distant cousins. One cousin harbors the mutation in a homozygous state, while the other carries a single copy of the mutation. A second mutation, 1594insA, which creates a stop signal two amino acids downstream at codon 535, was identified in the latter individual thereby resulting in a compound heterozygous state.

TABLE 1

Summary of mutations found in six Alström syndrome kindreds

| | Kindred | Mutations/ Affected subjects | Number of control chromosomes |
|---|---|---|---|
| 3737ins(n)$_{19}$ | 1 | 10/5 | 200 |
| 1582C>T | 57 | 2/1 | |
| 3808GA>Tdel; 3813G>A | 22 | 6/3 | |
| 3974delC | 42 | 2/1 | |
| 3974delC | 3 | 2/1 | |
| 4648C>T | 59 | 3/2 | |
| 1594insA | 59 | 1/2 | |

No mutations were observed in samples from the genera

A 3974delC mutation was observed in two unrelated young adults; a 19 year old male of British ancestry (K42, Subject A5) and a 21 year old male who traces his ancestry to Britain two centuries ago (K3, Subject A6). Both presented with infantile cardiomyopathy within the first two months of life and subsequently developed short stature, scoliosis, Type II diabetes mellitus, and renal insufficiency. However, these subjects differ in the course of their disease presentation. Subject K42 A5 experienced a sudden recurrence of dilated cardiomyopathy at age 18 and has no evidence of hepatic dysfunction. Subject K3 A6, however, presented with severe hepatic failure at age 20 but has not had a recurrence of cardiomyopathy. This finding of different disease progression in individuals carrying the same mutation suggests that the phenotypic variability seen in many Alström patients may be the result of genetic or environmental modifiers interacting with the ALMS1 locus.

Figure 4:
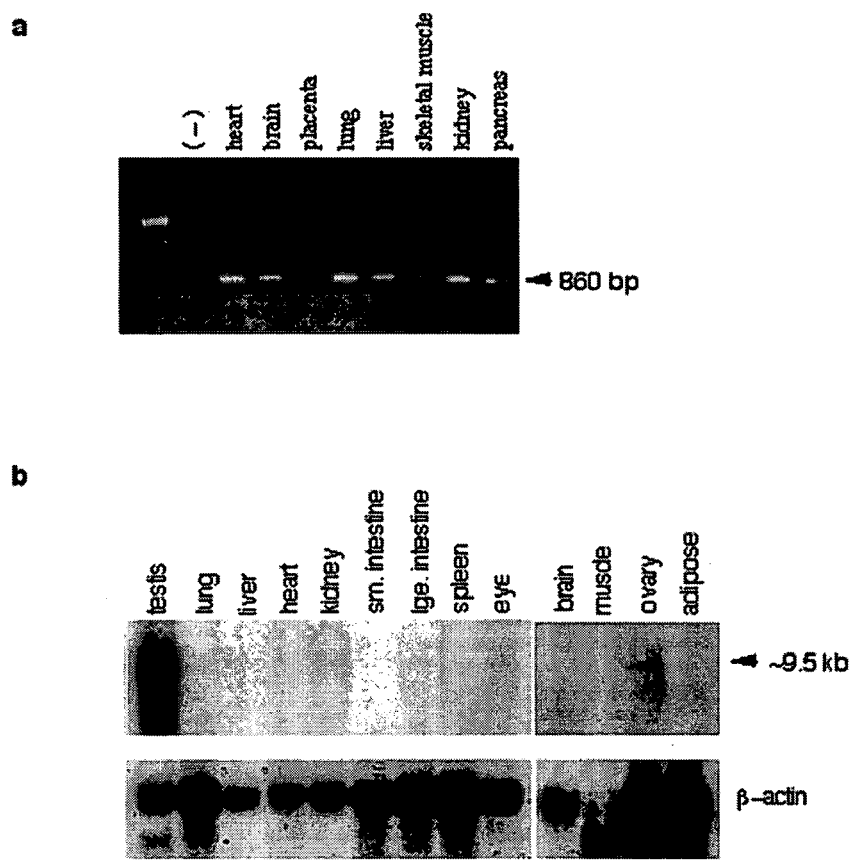
FIG. 4 Expression of ALMS1 in various adult human and mouse tissues. a, RT-PCR of human cDNA multiple tissue panel (CLONTECH). b, Mouse northern blot analysis of 5 ug polyA+ RNA hybridized with a 490 bp cDNA fragment spanning exons 1–3 and β-actin as control. Although ALMS1 expression in brain and muscle was not detected by human northern analysis, low expression was observed by RT-PCR.

Expression analysis was performed on mouse and human RNA. Probing a human multiple tissue blot (Ambion) with ALMS1 cDNA fragments failed to detect expression of ALMS1 after a 7 day exposure, suggesting low abundance of the transcript. However, RT-PCR of human cDNA panel 1 (CLONTECH) did show that ALMS1 is ubiquitously expressed (FIG. 4a). Northern analyses of mouse poly A+ RNA (5 µg) confirmed the ubiquitous but low expression in lung, heart, kidney, large intestine, spleen, eye, and ovary (FIG. 4b). In concordance with the abundance of ALMS1 in testis cDNA libraries indicated in the public and Incyte Genomics databases, a high level of expression was observed in mouse testis. Additional tissues, not tested by RT-PCR or northern analysis, that showed expression in human cDNA libraries from the Incyte Genomics database included adrenal, thyroid, pituitary, and mammary glands, thymus, uterus, urinary tract, colon, and connective tissue.

While no significant homology to other human genes in the NCBI database was identified, we were able to assemble the mouse Alms1 cDNA sequence (5.6 kb) from alignments of several EST sequences (GenBank & TIGR) as well as by aligning the human cDNA sequence with mouse genomic trace data (GenBank) and mouse genomic fragments (Celera). The mouse cDNA sequence was confirmed by sequencing PCR-amplified mouse Alms1 cDNA in C57BL6/J mice (GenBank, AF425257). The deduced amino acid sequence is 67.3% identical to the human ALMS1 protein sequence.

In an attempt to deduce the function of ALMS1, motif and homology searches were performed using Prosite and Pfam databases. No signal sequences or transmembrane regions were detected, which together with an overall hydrophilic nature of the protein suggests an intracellular location. A leucine zipper motif (PS00029, aa213–234) and a serine rich region (aa1590–1606) were found in the predicted human protein. In addition, potential nuclear localization signals (PS50079, aa1538–1563 and 1670–1687), as well as a histidine rich region (aa1219–1256) were identified in the mouse sequence. All of these features are conserved between human and mouse ALMS1; however, because of the frequent occurrence of these motifs in various proteins, the functional significance of these matches has to be tested experimentally. In addition to the above domains, a 120 amino acid region at the C-terminus of ALMS1 was identified that showed sequence similarity to regions of two predicted proteins from macaque (AB055273) and mouse (AK016590). Due to the relatively small region of homology, it is unlikely that these sequences represent additional gene family members. It is more likely that this well conserved ALMS1 motif defines a protein domain that may have structural or functional significance (FIG. 5).

Obesity and type 2 diabetes, pervasive public health problems, are associated with increased risk of morbidity and mortality and affect a large percentage of the population[13]. Both diseases are influenced by environmental conditions but also by a strong genetic component [14,15]. Interestingly, most of the genes identified to date that lead to obesity and type 2 diabetes have been in the context of syndromic diseases such as Bardet-Biedl Syndrome[16,17,18]. The infantile obesity observed in Alström patients is most likely a primary consequence of the alteration of the Alström gene as they constitute an earlier (as early as 6 months of age) phenotype observed in all affected children. The sequelae of insulin resistance and chronic hyperglycemia accompanied by secondary complications such as hyperlipidemia and atherosclerosis, observed in Alström Syndrome, are conditions observed in common forms of adult-onset type 2 diabetes, with the difference being that they occur at an accelerated rate in Alström patients. This suggests that ALMS1 may lie in the same or parallel pathway as obesity associated NIDDM. Determining the function of the ALMS1 gene will potentially provide insights into how this gene interacts with other genes to produce its pathological effects. Although it is unlikely that mutations within ALMS1 play a major role in common diseases in the general population, the real value of studying this gene lies in the access it may provide to novel metabolic and regulatory pathways involved in the etiology of obesity, type 2 diabetes, neurosensory diseases and related disorders. Many examples of this paradigm of identification of single gene mutations that have allowed for the identification of the upstream and downstream molecules in a biological pathway are available in the literature (i.e. leptin and the Jak/Stat kinase pathway in obesity[19]).

Another aspect of the invention pertains to vectors, preferably expression vectors, containing a nucleic acid encoding an ALMS1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A host cell of the invention, such as a prokaryotic or eukaryotic host cell in culture, can be used to produce (i.e., espress) an ALMS1 protein. Accordingly, the invention further provides methods for producing an ALMS1 protein using the host cells of the invention. In one embodiment, the method comprises culturing the host cell of the invention (into which, for example, a recombinant expression vector encoding an ALMS1 protein has been introduced) in a suitable medium such that an ALMS1 protein is produced. In another embodiment, the method further comprises isolating an ALMS1 protein from the medium or the host cell.

Methods

Families. DNA from Alström family members and control subjects was isolated from peripheral whole blood using a standard protocol[20]. Inclusion criteria were based upon the assessment of the cardinal features of ALMS as well as the clinical diagnosis. Written informed consent was obtained from all subjects. All protocols were pre-approved by the Internal Review Board at The Jackson Laboratory.

Genotyping. Oligonucleotide primers for amplification of short tandem repeat polymorphisms (STRPs) were either obtained from Research Genetics or designed (MacVector 6.0)[21] and custom made (One Trick Pony). PCR amplification of STRPs was performed with $^{33}$P-labeled oligonucleotides as previously described[22]. PCR products were separated on a 6% denaturing polyacrylamide gel and visualized by autoradiography.

Mutation analysis. Sixteen exons of ALMS1 were PCR-amplified by standard PCR protocols. Amplified products were separated on a 1–1.2% gel, excised and purified using Nucleospin columns (CLONTECH) and sequenced (ABI Prism 3700). Sequencing results were compared to an unaffected control, BAC sequence (AC069346 and AC074008) and cDNA (KIAA0328).

Mouse cDNA sequence. Total RNA was prepared from whole brain of male C57BL/6J mice. Tissues were homogenized and RNA was isolated by treatment with TRIzol (Life Technologies) according to the manufacturer's protocol. cDNA was generated using the Superscript One-Step RT-PCR kit (Life Technologies). Primers for PCR-amplification of Alms1 were designed from sequences of aligned ESTs from Celera database. PCR-amplifcation of cDNA was performed using the Expand Template system (Roche).

Expression analysis. Mouse Northern: To generate the probe for northern analysis, mouse C57BL/6J retinal cDNA was PCR-amplified with exon 1-specific primers (forward: 5'-TTCAGACTCTCTTGATGGAAGC-3' (SEQ ID NO: 69) and reverse 5'-TTGTTGTCCCATGAGCAGC-3' (SEQ ID NO: 70)) using the Expand Template system (Roche). The 394 bp product was purified and radiolabeled (Rediprime II labelling system, Amersham Pharmacia). Mouse multiple tissue blots[23] were pre-hybridized for one hour with Rapid Hyb buffer (Amersham Pharmacia) and hybridization was performed overnight. Membranes were washed and hybridized products were visualized by autoradiography following an 8 day exposure. Blots were probed with β-actin as a control[23]. Human Northern: A human multiple tissue blot (FirstChoice Blot 1, Ambion) was hybridized with a 490 bp probe generated by PCR amplification of genomic DNA (Primers: for 5'-TATGGCACTGAAACGATGC-3' (SEQ ID NO: 71) and rev 5'-TTTATTCCCAATGGTTCCACT-3' (SEQ ID NO: 72)). Hybridization was performed as above. RT-PCR: Human multiple tissue cDNA panel I (CLONTECH) was PCR-amplified using forward primer 5'-TGTACTGGAGCATCTGTGGG-3' (SEQ ID NO: 73) and reverse primer 5'-CAGTGATTTGGGGCTGACTG-3' (SEQ ID NO: 74) for 35 cycles at an annealing temperature of 56° C.

GenBank accession numbers. Sequence data for human transcript KIAA0328, AB002326, mouse C57BL6/J cDNA, AF425257 and human BACs, AC069346 and AC074008.

Discovery of ALMS1 and its link to Alström Syndrome allows improved diagnosis of Alström Syndrome. Patients can be tested for Alström Syndrome in a number of new ways using this information. Genetic material (particularly genomic DNA or mRNA) can be isolated from the patients and sequenced by known methods to determine the presence of any mutations in the coding sequence of the ALMS1 gene, which would indicate Alström Syndrome. Furthermore, the DNA sequence of ALMS1, its complement strand or sequences which hybridize to the DNA sequence of ALMS1 or its complement strand under stringent conditions could be used in a Northern blot analysis to test transcription levels of the gene. Below normal transcription levels of the gene could be used to diagnose Alström Syndrome, since a lack of transcription would indicate that insufficient functional ALMS1 gene product is present in the tissues. Lastly, the protein encoded by ALMS1 could be expressed and isolated and an antibody specific to that protein could be obtained by standard methods of biotechnology. The antibody would then be useful to detect the presence or absence of the ALMS1 protein in tissue samples from patients. Insufficient ALMS1 protein would implicate Alström Syndrome. All of the above methods can be practiced by those of skill in the art, once they know of the sequence of ALMS1 and the link between ALMS1 and Alström Syndrome.

The term "hybridize under stringent conditions" means that two nucleic acid fragments are capable of hybridization to one another under standard hybridization conditions described in Sambrook et al., Molecular Cloning: A Laboratory Manual (1989) Cold Spring Harbor Laboratory Press, New York, USA. More specifically, "stringent conditions" as used herein refer to hybridization at 65° C. in a hybridization buffer consisting of 250 mmol/l sodium phosphate buffer pH 7.2, 7% (w/v) SDS, 1% (w/v) BSA, 1 mmol/l EDTA and 0.1 mg/ml single-stranded salmon sperm DNA. A final wash is performed at 65° C. in 125 mmol/l sodium phosphate buffer pH 7.2, 1 mmol/l EDTA and 1% (w/v) SDS.

REFERENCES CITED

The references listed below are incorporated herein by reference to the extent that they supplement, explain, provide a background for or teach methodology, techniques and/or compositions employed herein.

1. Gloyn A L, McCarthy M I. The genetics of type 2 diabetes. *Best Pract Res Clin Endocrinol Metab* 15, 293–308 (2001).
2. Boutin P, Froguel P. Genetics of human obesity. *Best Pract Res Clin Endocrinol Metab* 15, 391–404 (2001)
3. Alström, C. H., Hallgren, B., Nilsson, L. B. & Asander, H. Retinal degeneration combined with obesity, diabetes mellitus and neurogenous deafness. A specific syndrome (not hitherto described) distinct from Laurence-Moon-Biedl syndrome. A clinical endocrinological and genetic examination based on a large pedigree. *Acta Phychiatr Neurol Scand* 34 (Supplement 129), 1–35 (1959).
4. Goldstein, J. L. & Fialkow, P. J. The Alström syndrome. Report of three cases with further delineation of the clinical, pathophysiological, and genetic aspects of the disorder. *Medicine Baltimore* 52, 53–71 (1973).
5. Michaud, J. L. et al. Natural history of Alström syndrome in early childhood: Onset with dilated cardiomyopathy. *J Ped* 128, 225–229 (1996).
6. Connolly, M. B. et al. Hepatic dysfunction in Alström Disease. *Am J Med Genet* 40, 421–424 (1991).
7. Charles, S. J., Moore, A. T., Yates, J. R., Green, T. & Clark, P. Alström's syndrome: further evidence of autosomal recessive inheritance and endocrinological dysfunction. *J Med Genet* 27, 590–592 (1990).
8. Collin, G. B., Marshall, J. D., Cardon, L. R. & Nishina, P. M. Homozygosity mapping of Alström syndrome to chromosome 2p. *Hum-Mol-Genet* 6, 213–219 (1997).
9. Collin, G. B. et al. Alström syndrome: further evidence for linkage to human chromosome 2p13. *Hum Genet* 105, 474–479 (1999).
10. Macari, F. et al. Refinement of genetic localization of the Alström syndrome on chromosome 2p12–13 by linkage analysis in a North African family. *Hum Genet* 103, 658–661 (1998).
11. Williams, G. W., Woolard, P. M. & Hingamp, P. Nix: A nucleotide identification system at the "HGMP-RC" URL http://www.hgmp.mrc.ac.uk/NIX/ (1998).
12. Marshall, J. D. et al. Genealogy, natural history, and phenotype of Alström syndrome in a large Acadian kindred and three additional families. *Am J Med Genet* 73, 150–161 (1997).
13. Kopelman, P. G. Obesity as a medical problem. *Nature* 404, 635–643. (2000).
14. Froguel, P. & Velho, G. Genetic determinants of type 2 diabetes. *Recent Prog Horm Res* 56, 91–105 (2001).

15. Naggert, J., Harris, T. & North, M. The genetics of obesity. *Curr Opin Genet Dev* 7, 398–404 (1997).
16. Slavotinek, A. M. et al. Mutations in MKKS cause Bardet-Biedl syndrome. *Nat Genet* 26, 15–16 (2000).
17. Mykytyn, K. et al. Identification of the gene that, when mutated, causes the human obesity syndrome BBS4. *Nat Genet* 28, 188–191 (2001).
18. Nishimura, D. Y. et al. Positional cloning of a novel gene on chromosome 16q causing Bardet-Biedl syndrome (BBS2). *Hum Mol Genet* 10, 865–874 (2001).
19. Inui, A. Feeding and body-weight regulation by hypothalamic neuropeptides—mediation of the actions of leptin. *Trends Neurosci* 22, 62–67 (1999).
20. Kunkel, L. M., et al. Analysis of human Y-chromosome-specific reiterated DNA in chromosome variants. *Proc Natl Acad Sci USA* 74, 1245–1249 (1977).
21. Rastogi, P. A. MacVector. Integrated sequence analysis for the Macintosh. *Methods Mol Biol* 132, 47–69 (2000).
22. Collin, G. B. et al. Physical and genetic mapping of novel microsatellite polymorphisms on human chromosome 19. *Genomics* 37, 125–130 (1996).
23. Nishina, P. M., North, M. A., Ikeda, A., Yan, Y. & Naggert, J. K. Molecular characterization of a novel tubby gene family member, TULP3, in mouse and humans. *Genomics* 54, 215–220 (1998).

We claim:

1. An isolated polypeptide comprising an amino acid sequence selected from the group consisting of
   the amino acid sequence of SEQ ID NO:2,
   the amino acid sequence encoded by the nucleic acid molecule having the nucleotide sequence SEQ ID NO:1,
   and
   the amino acid sequence encoded by the nucleic acid molecule having nucleotide sequences encoding a polypeptide comprising the amino acid sequence of SEQ ID NO:2.

* * * * *

UNITED STATES PATENT AND TRADEMARK OFFICE
CERTIFICATE OF CORRECTION

PATENT NO. : 7,196,171 B2 Page 1 of 1
APPLICATION NO. : 10/973045
DATED : March 27, 2007
INVENTOR(S) : Collin et al.

It is certified that error appears in the above-identified patent and that said Letters Patent is hereby corrected as shown below:

On the Title Page (54) and Col. 1 line 1 and 3:
please delete "ALSTRÖEM" and insert --ALSTRÖM--

On the Title Page (75) line 3:
please delete "Vverona" and insert -- Verona --

Signed and Sealed this

Twentieth Day of November, 2007

JON W. DUDAS
*Director of the United States Patent and Trademark Office*